US008347891B2

(12) United States Patent
Demarais et al.

(10) Patent No.: US 8,347,891 B2
(45) Date of Patent: Jan. 8, 2013

(54) METHODS AND APPARATUS FOR PERFORMING A NON-CONTINUOUS CIRCUMFERENTIAL TREATMENT OF A BODY LUMEN

(75) Inventors: Denise Demarais, Los Gatos, CA (US); Hanson Gifford, III, Woodside, CA (US); Mark Deem, Mountain View, CA (US); Nicolas Zadno, Fremont, CA (US); Benjamin J. Clark, Redwood City, CA (US); Andrew Wu, Foster City, CA (US); Kenneth J. Michlitsch, Livermore, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 1014 days.

(21) Appl. No.: 11/599,890

(22) Filed: Nov. 14, 2006

(65) Prior Publication Data
US 2007/0129720 A1 Jun. 7, 2007

Related U.S. Application Data

(63) Continuation-in-part of application No. 11/129,765, filed on May 13, 2005, which is a continuation-in-part of application No. 10/408,665, filed on Apr. 8, 2003, now Pat. No. 7,162,303, application No. 11/599,890, which is a continuation-in-part of application No. 11/189,563, filed on Jul. 25, 2005, which is a continuation-in-part of application No. 11/129,765, filed on May 13, 2005, said application No. 11/189,563 is a continuation-in-part of application No. 10/900,199, filed on Jul. 28, 2004, now Pat. No. 6,978,174, which is a continuation-in-part of application No. 10/408,665, filed on Apr. 8, 2003, now Pat. No. 7,162,303.

(60) Provisional application No. 60/370,190, filed on Apr. 8, 2002, provisional application No. 60/415,575, filed on Oct. 3, 2002, provisional application No. 60/442,970, filed on Jan. 29, 2003, provisional application No. 60/616,254, filed on Oct. 5, 2004, provisional application No. 60/624,793, filed on Nov. 2, 2004.

(51) Int. Cl.
*A61B 18/12* (2006.01)
(52) U.S. Cl. ............... 128/898; 606/2; 606/52; 607/88; 607/101
(58) Field of Classification Search .............. 606/41–50; 128/898
See application file for complete search history.

(56) References Cited

U.S. PATENT DOCUMENTS 2,130,758 A  9/1938  Rose
(Continued)

FOREIGN PATENT DOCUMENTS
DE 3151180 A1 8/1982
(Continued)

OTHER PUBLICATIONS

U.S. Appl. No. 10/408,665, filed Apr. 8, 2003, Levin et al.
(Continued)

*Primary Examiner* — Aaron Roane

(57) ABSTRACT

Methods and apparatus are provided for non-continuous circumferential treatment of a body lumen. Apparatus may be positioned within a body lumen of a patient and may deliver energy at a first lengthwise and angular position to create a less-than-full circumferential treatment zone at the first position. The apparatus also may deliver energy at one or more additional lengthwise and angular positions within the body lumen to create less-than-full circumferential treatment zone(s) at the one or more additional positions that are offset lengthwise and angularly from the first treatment zone. Superimposition of the first treatment zone and the one or more additional treatment zones defines a non-continuous circumferential treatment zone without formation of a continuous circumferential lesion. Various embodiments of methods and apparatus for achieving such non-continuous circumferential treatment are provided.

22 Claims, 11 Drawing Sheets

U.S. PATENT DOCUMENTS

| | | |
|---|---|---|
| 2,276,995 A | 3/1942 | Milinowski |
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,472,406 A | 12/1995 | de la Torre et al. |
| 5,478,303 A | 12/1995 | Foley-Nolan et al. |
| 5,494,822 A | 2/1996 | Sadri |
| 5,498,238 A | 3/1996 | Shapland et al. |
| 5,499,971 A | 3/1996 | Shapland et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,575,810 A * | 11/1996 | Swanson et al. ............... 607/99 |
| 5,584,863 A | 12/1996 | Rauch et al. |
| 5,589,192 A | 12/1996 | Okabe et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,723,001 A | 3/1998 | Pilla et al. |
| 5,725,563 A | 3/1998 | Klotz et al. |
| 5,728,396 A | 3/1998 | Peery et al. |
| 5,741,248 A * | 4/1998 | Stern et al. ................... 606/21 |
| 5,747,060 A | 5/1998 | Sackler et al. |
| 5,755,750 A | 5/1998 | Petruska et al. |
| 5,756,115 A | 5/1998 | Moo-Young et al. |
| 5,769,880 A * | 6/1998 | Truckai et al. ............... 607/101 |
| 5,792,187 A | 8/1998 | Adams |
| 5,800,464 A | 9/1998 | Kieval |
| 5,807,306 A | 9/1998 | Shapland et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |

| Patent | Kind | Date | Inventors | Class |
|---|---|---|---|---|
| 5,861,021 | A | 1/1999 | Thome et al. | |
| 5,865,787 | A | 2/1999 | Shapland et al. | |
| 5,871,449 | A | 2/1999 | Brown | |
| 5,871,523 | A * | 2/1999 | Fleischman et al. | 607/99 |
| 5,891,181 | A | 4/1999 | Zhu | |
| 5,906,636 | A | 5/1999 | Casscells, III et al. | |
| 5,906,817 | A | 5/1999 | Moullier et al. | |
| 5,913,876 | A | 6/1999 | Taylor et al. | |
| 5,916,154 | A | 6/1999 | Hobbs et al. | |
| 5,916,239 | A | 6/1999 | Geddes et al. | |
| 5,919,187 | A | 7/1999 | Guglielmi et al. | |
| 5,924,997 | A | 7/1999 | Campbell | |
| 5,928,272 | A | 7/1999 | Adkins et al. | |
| 5,935,075 | A | 8/1999 | Casscells et al. | |
| 5,944,710 | A | 8/1999 | Dev et al. | |
| 5,983,131 | A | 11/1999 | Weaver et al. | |
| 5,983,141 | A | 11/1999 | Sluijter et al. | |
| 6,006,134 | A | 12/1999 | Hill et al. | |
| 6,010,613 | A | 1/2000 | Walters et al. | |
| 6,026,326 | A | 2/2000 | Bardy | |
| 6,051,017 | A | 4/2000 | Loeb et al. | |
| 6,058,328 | A | 5/2000 | Levine et al. | |
| 6,058,331 | A | 5/2000 | King | |
| 6,073,048 | A | 6/2000 | Kieval et al. | |
| 6,077,227 | A | 6/2000 | Miesel et al. | |
| 6,086,527 | A | 7/2000 | Talpade | |
| 6,117,101 | A * | 9/2000 | Diederich et al. | 604/22 |
| 6,122,548 | A | 9/2000 | Starkebaum et al. | |
| 6,123,718 | A | 9/2000 | Tu et al. | |
| 6,146,379 | A * | 11/2000 | Fleischman et al. | 606/41 |
| 6,146,380 | A | 11/2000 | Racz et al. | |
| 6,161,048 | A | 12/2000 | Sluijter et al. | |
| 6,171,306 | B1 * | 1/2001 | Swanson et al. | 606/41 |
| 6,178,349 | B1 | 1/2001 | Kieval | |
| 6,192,889 | B1 | 2/2001 | Morrish | |
| 6,205,361 | B1 | 3/2001 | Kuzma et al. | |
| 6,208,894 | B1 | 3/2001 | Schulman et al. | |
| 6,214,032 | B1 | 4/2001 | Loeb et al. | |
| 6,219,577 | B1 | 4/2001 | Brown, III et al. | |
| 6,224,592 | B1 * | 5/2001 | Eggers et al. | 606/32 |
| 6,238,702 | B1 | 5/2001 | Berde et al. | |
| 6,245,026 | B1 | 6/2001 | Campbell et al. | |
| 6,251,130 | B1 | 6/2001 | Dobak, III et al. | |
| 6,258,087 | B1 * | 7/2001 | Edwards et al. | 606/41 |
| 6,259,952 | B1 | 7/2001 | Sluijter et al. | |
| 6,269,269 | B1 | 7/2001 | Ottenhoff et al. | |
| 6,272,377 | B1 | 8/2001 | Sweeney et al. | |
| 6,272,383 | B1 | 8/2001 | Grey et al. | |
| 6,273,886 | B1 * | 8/2001 | Edwards et al. | 606/34 |
| 6,280,377 | B1 | 8/2001 | Talpade | |
| 6,287,304 | B1 | 9/2001 | Eggers et al. | |
| 6,287,608 | B1 | 9/2001 | Levin et al. | |
| 6,292,695 | B1 | 9/2001 | Webster, Jr. et al. | |
| 6,304,777 | B1 | 10/2001 | Ben-Haim et al. | |
| 6,304,787 | B1 | 10/2001 | Kuzma et al. | |
| 6,306,423 | B1 | 10/2001 | Donovan et al. | |
| 6,322,559 | B1 | 11/2001 | Daulton et al. | |
| 6,325,798 | B1 * | 12/2001 | Edwards et al. | 606/41 |
| 6,326,020 | B1 | 12/2001 | Kohane et al. | |
| 6,326,177 | B1 | 12/2001 | Schoenbach et al. | |
| 6,334,069 | B1 | 12/2001 | George et al. | |
| 6,347,247 | B1 | 2/2002 | Dev et al. | |
| 6,353,763 | B1 | 3/2002 | George et al. | |
| 6,355,031 | B1 * | 3/2002 | Edwards et al. | 606/31 |
| 6,356,786 | B1 | 3/2002 | Rezai et al. | |
| 6,356,787 | B1 | 3/2002 | Rezai et al. | |
| 6,366,808 | B1 | 4/2002 | Schroeppel et al. | |
| 6,366,815 | B1 | 4/2002 | Haugland et al. | |
| 6,383,151 | B1 * | 5/2002 | Diederich et al. | 601/2 |
| 6,393,324 | B2 | 5/2002 | Gruzdowich et al. | |
| 6,400,982 | B2 | 6/2002 | Sweeney et al. | |
| 6,402,744 | B2 * | 6/2002 | Edwards et al. | 606/41 |
| 6,402,746 | B1 * | 6/2002 | Whayne et al. | 606/41 |
| 6,405,079 | B1 | 6/2002 | Ansarinia | |
| 6,405,732 | B1 | 6/2002 | Edwards et al. | |
| 6,415,183 | B1 | 7/2002 | Scheiner et al. | |
| 6,415,187 | B1 | 7/2002 | Kuzma et al. | |
| 6,423,058 | B1 * | 7/2002 | Edwards et al. | 606/41 |
| 6,438,423 | B1 | 8/2002 | Rezai et al. | |
| 6,442,424 | B1 | 8/2002 | Ben-Haim et al. | |
| 6,447,506 | B1 * | 9/2002 | Swanson et al. | 606/41 |
| 6,449,507 | B1 | 9/2002 | Hill et al. | |
| 6,450,942 | B1 | 9/2002 | Lapanashvili et al. | |
| 6,461,314 | B1 | 10/2002 | Pant et al. | |
| 6,464,687 | B1 | 10/2002 | Ishikawa et al. | |
| 6,464,697 | B1 * | 10/2002 | Edwards et al. | 606/41 |
| 6,471,699 | B1 * | 10/2002 | Fleischman et al. | 606/41 |
| 6,473,644 | B1 | 10/2002 | Terry, Jr. et al. | |
| 6,482,619 | B1 | 11/2002 | Rubinsky et al. | |
| 6,492,762 | B1 * | 12/2002 | Pant et al. | 310/334 |
| 6,500,174 | B1 | 12/2002 | Maguire et al. | |
| 6,508,774 | B1 | 1/2003 | Acker et al. | |
| 6,514,226 | B1 | 2/2003 | Levin et al. | |
| 6,514,246 | B1 * | 2/2003 | Swanson et al. | 606/41 |
| 6,516,211 | B1 | 2/2003 | Acker et al. | |
| 6,522,926 | B1 | 2/2003 | Kieval et al. | |
| 6,522,932 | B1 | 2/2003 | Kuzma et al. | |
| 6,524,607 | B1 | 2/2003 | Goldenheim et al. | |
| 6,534,081 | B2 | 3/2003 | Goldenheim et al. | |
| 6,536,949 | B1 | 3/2003 | Heuser | |
| 6,551,310 | B1 * | 4/2003 | Ganz et al. | 606/41 |
| 6,562,034 | B2 * | 5/2003 | Edwards et al. | 606/41 |
| 6,564,096 | B2 | 5/2003 | Mest | |
| 6,571,127 | B1 | 5/2003 | Ben-Haim et al. | |
| 6,592,567 | B1 | 7/2003 | Levin et al. | |
| 6,599,256 | B1 | 7/2003 | Acker et al. | |
| 6,600,954 | B2 | 7/2003 | Cohen et al. | |
| 6,600,956 | B2 | 7/2003 | Maschino et al. | |
| 6,601,459 | B1 | 8/2003 | Jenni et al. | |
| 6,605,084 | B2 | 8/2003 | Acker et al. | |
| 6,615,071 | B1 | 9/2003 | Casscells, III et al. | |
| 6,616,624 | B1 | 9/2003 | Kieval | |
| 6,620,151 | B2 | 9/2003 | Blischak et al. | |
| 6,622,041 | B2 | 9/2003 | Terry, Jr. et al. | |
| 6,635,054 | B2 * | 10/2003 | Fjield et al. | 606/27 |
| 6,645,201 | B1 * | 11/2003 | Utley et al. | 606/41 |
| 6,666,845 | B2 | 12/2003 | Hooper et al. | |
| 6,669,655 | B1 | 12/2003 | Acker et al. | |
| 6,669,691 | B1 * | 12/2003 | Taimisto | 606/41 |
| 6,671,533 | B2 * | 12/2003 | Chen et al. | 600/374 |
| 6,671,556 | B2 | 12/2003 | Osorio et al. | |
| 6,672,312 | B2 * | 1/2004 | Acker | 128/898 |
| 6,676,657 | B2 | 1/2004 | Wood | |
| 6,681,136 | B2 | 1/2004 | Schuler et al. | |
| 6,684,105 | B2 | 1/2004 | Cohen et al. | |
| 6,690,971 | B2 | 2/2004 | Schauerte et al. | |
| 6,692,738 | B2 | 2/2004 | MacLaughlin et al. | |
| 6,697,670 | B2 | 2/2004 | Chomenky et al. | |
| 6,712,074 | B2 * | 3/2004 | Edwards et al. | 128/898 |
| 6,712,814 | B2 * | 3/2004 | Edwards et al. | 606/41 |
| 6,718,208 | B2 | 4/2004 | Hill et al. | |
| 6,728,563 | B2 * | 4/2004 | Rashidi | 600/374 |
| 6,735,471 | B2 | 5/2004 | Hill et al. | |
| 6,738,663 | B2 | 5/2004 | Schroeppel et al. | |
| 6,740,040 | B1 * | 5/2004 | Mandrusov et al. | 600/439 |
| 6,746,465 | B2 * | 6/2004 | Diederich et al. | 606/192 |
| 6,749,598 | B1 | 6/2004 | Keren et al. | |
| 6,761,716 | B2 * | 7/2004 | Kadhiresan et al. | 606/34 |
| 6,780,183 | B2 | 8/2004 | Jimenez, Jr. et al. | |
| 6,786,904 | B2 | 9/2004 | Doscher et al. | |
| 6,795,728 | B2 | 9/2004 | Chornenky et al. | |
| 6,845,267 | B2 | 1/2005 | Harrison et al. | |
| 6,850,801 | B2 | 2/2005 | Kieval et al. | |
| 6,865,416 | B2 | 3/2005 | Dev et al. | |
| 6,869,431 | B2 | 3/2005 | Maguire et al. | |
| 6,872,206 | B2 * | 3/2005 | Edwards et al. | 606/41 |
| 6,885,888 | B2 | 4/2005 | Rezai | |
| 6,916,656 | B2 | 7/2005 | Walters et al. | |
| 6,920,883 | B2 * | 7/2005 | Bessette et al. | 128/898 |
| 6,927,049 | B2 | 8/2005 | Rubinsky et al. | |
| 6,939,345 | B2 | 9/2005 | KenKnight et al. | |
| 6,958,060 | B2 | 10/2005 | Mathiesen et al. | |
| 6,971,394 | B2 * | 12/2005 | Sliwa et al. | 128/898 |
| 6,972,013 | B1 | 12/2005 | Zhang et al. | |
| 6,978,174 | B2 | 12/2005 | Gelfand et al. | |
| 6,985,774 | B2 | 1/2006 | Kieval et al. | |
| 6,994,700 | B2 | 2/2006 | Elkins et al. | |
| 6,994,706 | B2 | 2/2006 | Chornenky et al. | |

| | | | |
|---|---|---|---|
| 7,001,336 B2 * | 2/2006 | Mandrusov et al. .......... 600/439 |
| 7,048,734 B1 * | 5/2006 | Fleischman et al. ............ 606/42 |
| 7,054,685 B2 | 5/2006 | Dimmer et al. |
| 7,063,679 B2 | 6/2006 | Maguire et al. |
| 7,063,696 B2 * | 6/2006 | Taimisto ........................ 606/41 |
| 7,081,114 B2 | 7/2006 | Rashidi |
| 7,081,115 B2 | 7/2006 | Taimisto |
| 7,083,614 B2 * | 8/2006 | Fjield et al. ..................... 606/41 |
| 7,115,122 B1 * | 10/2006 | Swanson et al. ................ 606/41 |
| 7,122,019 B1 | 10/2006 | Kesten et al. |
| 7,122,031 B2 * | 10/2006 | Edwards et al. ................ 606/34 |
| 7,294,143 B2 * | 11/2007 | Francischelli ................ 607/105 |
| 7,303,560 B2 * | 12/2007 | Chin et al. ....................... 606/41 |
| 7,306,593 B2 * | 12/2007 | Keidar et al. ................... 606/34 |
| 7,326,201 B2 * | 2/2008 | Fjield et al. ..................... 606/27 |
| 7,329,254 B2 * | 2/2008 | West et al. ...................... 606/41 |
| 7,367,974 B2 * | 5/2008 | Haemmerich et al. ......... 606/41 |
| 7,413,568 B2 * | 8/2008 | Swanson et al. ................ 606/41 |
| 7,419,486 B2 * | 9/2008 | Kampa ............................ 606/32 |
| 7,422,587 B2 * | 9/2008 | Bek et al. ........................ 606/41 |
| 7,476,235 B2 * | 1/2009 | Diederich et al. ............. 606/192 |
| 7,507,234 B2 * | 3/2009 | Utley et al. ..................... 606/21 |
| 7,507,238 B2 * | 3/2009 | Edwards et al. ................ 606/41 |
| 7,524,318 B2 * | 4/2009 | Young et al. .................... 606/41 |
| 7,556,628 B2 * | 7/2009 | Utley et al. ..................... 606/41 |
| 7,699,844 B2 * | 4/2010 | Utley et al. ..................... 606/41 |
| 7,717,948 B2 * | 5/2010 | Demarais et al. ............... 607/96 |
| 7,824,402 B2 * | 11/2010 | Vaska et al. ..................... 606/41 |
| 7,837,681 B2 * | 11/2010 | Whayne et al. ................. 606/41 |
| 7,850,685 B2 * | 12/2010 | Kunis et al. ..................... 606/41 |
| 7,959,627 B2 * | 6/2011 | Utley et al. ..................... 606/41 |
| 2001/0044596 A1 | 11/2001 | Jaafar |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065512 A1 * | 5/2002 | Fjield et al. ..................... 606/27 |
| 2002/0068885 A1 * | 6/2002 | Harhen et al. ..................... 601/3 |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0040774 A1 | 2/2003 | Terry et al. |
| 2003/0045909 A1 | 3/2003 | Gross et al. |
| 2003/0050632 A1 * | 3/2003 | Fjield et al. ..................... 606/27 |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0150464 A1 | 8/2003 | Casscells |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0147811 A1 * | 7/2004 | Diederich et al. ............. 600/207 |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 * | 9/2004 | Sinelnikov et al. ............. 606/27 |
| 2004/0193228 A1 | 9/2004 | Gerber |
| 2004/0220511 A1 | 11/2004 | Scott et al. |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0009753 A1 * | 1/2006 | Fjield et al. ..................... 606/27 |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0100667 A1 | 5/2006 | Machado et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2007/0265687 A1 | 11/2007 | Deem et al. |
| 2008/0213331 A1 | 9/2008 | Gelfand et al. |
| 2008/0255642 A1 | 10/2008 | Zarins et al. |

| | | | |
|---|---|---|---|
| 2009/0036948 | A1 | 2/2009 | Levin et al. |
| 2009/0062873 | A1 | 3/2009 | Wu et al. |
| 2009/0076409 | A1 | 3/2009 | Wu et al. |
| 2010/0010567 | A1 | 1/2010 | Deem et al. |
| 2010/0057150 | A1 | 3/2010 | Demarais et al. |
| 2010/0137860 | A1 | 6/2010 | Demarais et al. |
| 2010/0137952 | A1 | 6/2010 | Demarais et al. |
| 2010/0168731 | A1 | 7/2010 | Wu et al. |
| 2010/0168739 | A1 | 7/2010 | Wu et al. |
| 2010/0174282 | A1 | 7/2010 | Demarais et al. |
| 2010/0191112 | A1 | 7/2010 | Demarais et al. |
| 2010/0222851 | A1 | 9/2010 | Deem et al. |
| 2010/0222854 | A1 | 9/2010 | Demarais et al. |
| 2010/0249773 | A1 | 9/2010 | Clark et al. |
| 2010/0268307 | A1 | 10/2010 | Demarais et al. |

FOREIGN PATENT DOCUMENTS

| | | | |
|---|---|---|---|
| DE | 29909082 | U1 | 7/1999 |
| DE | 10252325 | A1 | 5/2004 |
| EP | 0811395 | A2 | 6/1997 |
| EP | 1009303 | B1 | 6/2009 |
| WO | WO-85/01213 | | 3/1985 |
| WO | WO-91/04725 | | 4/1991 |
| WO | WO-93/02740 | | 2/1993 |
| WO | WO-93/07803 | | 4/1993 |
| WO | WO 94/00188 | | 1/1994 |
| WO | WO-96/04957 | | 1/1995 |
| WO | WO-95/33514 | | 12/1995 |
| WO | WO-96/11723 | | 4/1996 |
| WO | WO-97/13550 | | 4/1997 |
| WO | WO-97/49453 | | 12/1997 |
| WO | WO-98/37926 | | 9/1998 |
| WO | WO-98/43700 | | 10/1998 |
| WO | WO-98/43701 | | 10/1998 |
| WO | WO-98/48888 | | 11/1998 |
| WO | WO-99/33407 | | 7/1999 |
| WO | WO-99/51286 | | 10/1999 |
| WO | WO-99/52424 | | 10/1999 |
| WO | WO-9962413 | A1 | 12/1999 |
| WO | WO-01/26729 | | 4/2001 |
| WO | WO-02/09808 | | 2/2002 |
| WO | WO-02/26314 | | 4/2002 |
| WO | WO-02/053207 | | 7/2002 |
| WO | WO-02/070039 | A2 | 9/2002 |
| WO | WO-02/070047 | | 9/2002 |
| WO | WO-02/085448 | | 10/2002 |
| WO | WO-03/018108 | | 3/2003 |
| WO | WO-03/028802 | | 4/2003 |
| WO | WO-03/063692 | | 8/2003 |
| WO | WO-03/071140 | A2 | 8/2003 |
| WO | WO-03/076008 | | 9/2003 |
| WO | WO-03/082080 | | 10/2003 |
| WO | WO-03/082403 | | 10/2003 |
| WO | WO-2004/026370 | | 4/2004 |
| WO | WO-2004/026371 | | 4/2004 |
| WO | WO-2004/026374 | | 4/2004 |
| WO | WO-2004/030718 | | 4/2004 |
| WO | WO-2004/032791 | | 4/2004 |
| WO | WO-2004/107965 | | 12/2004 |
| WO | WO-2005014100 | | 2/2005 |
| WO | WO-2005016165 | | 2/2005 |
| WO | WO 2005/032646 | | 4/2005 |
| WO | WO-2005/065284 | | 7/2005 |
| WO | WO-2005/084389 | A2 | 9/2005 |
| WO | WO-2005/097256 | A2 | 10/2005 |
| WO | WO-2005/123183 | | 12/2005 |
| WO | WO-2006/007048 | A2 | 1/2006 |
| WO | WO-2006018528 | A1 | 2/2006 |
| WO | WO-2006/031899 | A2 | 3/2006 |
| WO | WO-2006022790 | A1 | 3/2006 |
| WO | WO-2006041847 | | 4/2006 |
| WO | WO-2006041881 | | 4/2006 |
| WO | WO-2007035537 | | 3/2007 |
| WO | WO-2007078997 | A2 | 7/2007 |
| WO | WO-2007086965 | | 8/2007 |
| WO | WO-2007103879 | | 9/2007 |
| WO | WO-2007103881 | | 9/2007 |
| WO | WO-2007121309 | | 10/2007 |
| WO | WO-2007146834 | | 12/2007 |
| WO | WO-2008003058 | | 1/2008 |
| WO | WO-2008061150 | | 5/2008 |
| WO | WO-2008061152 | | 5/2008 |
| WO | WO-2008070413 | | 6/2008 |
| WO | WO-2010078175 | A1 | 7/2010 |

OTHER PUBLICATIONS

U.S. Appl. No. 10/900,199, filed Jul. 28, 2004, Gelfand.
U.S. Appl. No. 11/129,765, filed May 13, 2005, Deem.
U.S. Appl. No. 11/133,925, filed May 20, 2005, Gelfand.
U.S. Appl. No. 11/144,173, filed Jun. 3, 2005, Levin et al.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.
"2003 European Society of Hypertension—European Society of Cardiology guidelines for the management of arterial hypertension," Journal of Hypertension 2003, vol. 21, No. 6, pp. 1011-1053.
"Advances in the role of the sympathetic nervous system in cardiovascular medicine," 2001 SNS Report, No. 3, Springer, published with an educational grant from Servier, pp. 1-8.
"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.
"Electropermeabilization (Electroporation)," Cyto Pulse Sciences Inc., http://www.cytopulse.com/electroporation.html (last accessed Mar. 3, 2005), 3 pages.
"Electroporation based Technologies and Treatments," ESPE Newsletter No. 6, QLK 02002-2003, Jan. 2005, www.cliniporator.com, 4 pages.
"End-stage renal disease payment policies in traditional Medicare," Report to the Congress: Medicare Payment Policy, Mar. 2001, Medpac, pp. 123-138.
"Fact Book Fiscal Year 2003," National Institutes of Health National Heart, Lung, and Blood Institute, Feb. 2004, 197 pages.
"Heart Disease and Stroke Statistics—2004 update," American Heart Association, American Stroke Association, Dallas, Texas, © 2003 American Heart Association, 52 pages.
"Hypertension Incidence and Prevalence, Age Specific Rates, By Gender, B.C., 2001/2002," Graph., Chronic Disease Management, May 2003, British Columbia Ministry of Health Services, 1 page.
Implantable Pump—The Medtronic MiniMed 2007 Implantable Insulin Pump System, Medtronic MiniMed 2004, 4 pages.
"Isovue: Data Sheet". Regional Health Limited. 8 pages. Mar. 11, 2003.
"Market for infusion pumps grows with an aging population," NWL 97-01, The BBI Newsletter, vol. 20, No. 2, Feb. 1, 1997, American Health Consultants Inc., 6 pages.
"PHCL 762 Pharmacology of the Autonomic Nervous System," Chapter 2 and 6.8 in Mosby, http://www.kumc.edu/research/medicine/pharmacology/CAI/phcl762.html, last accessed Aug. 24, 2004, 14 pages.
"Programmable Infusion System," Pumps and Pump Selection, Medtronic Pain Therapies, Medtronic, Inc. Sep. 5, 2001, 2 pages.
"Pulmonary Concepts in Critical Care Breath Sounds," http://mbob.tripod.com/breath.htm, last accessed Aug. 23, 2004, 5 pages.
"Pulmonary Function Testing," http://jan.ucc.nau.edu/~daa/lecture/pft.htm, last accessed Aug. 23, 2004, 8 pages.
"Sensorcaine—MPF Spinal Injection," informational document, AstraZeneca 2001, 2 pages.
"Summary," Critical Reviews in Biomedical Engineering, vol. 17, Issue 5, 1989, pp. 515-529.
"The Antihypertensive and Lipid-Lowering Treatment to Prevent Heart Attack Trial," ALLHAT Research Group, JAMA 2002, vol. 288, pp. 2981-2997.
Aars, H. and S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.
Abramov, G.S. et al., "Alteration in sensory nerve function following electrical shock," Burns vol. 22, No. 8, © 1996 Elsevier Science Ltd., pp. 602-606.

Achar, Suraj, M.D. and Suriti Kundu, M.D., "Principles of Office Anesthesia: Part I. Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, © 1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, © 2004 Current Science Inc., pp. 34-40.

Alford, J.Winslow, M.D. and Paul. D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, © 2003 Arthroscopy Association of North America, pp. 855-861.

Amersham Health. "Hypaque-Cysto" 6 pages. 2003.

Andrews, B.T. et al., "The use of surgical sympathectomy in the treatment of chronic renal pain," Mar. 5, 1997, British Journal of Urology, vol. 80, © 1997 British Journal of Urology, pp. 6-10.

Antman, Elliott M. and Eugene Braunwald, "Chapter 37—Acute Myocardial Infarction," Heart Disease—A Textbook of Cardiovascular Medicine, 5th Edition, vol. 2, 1997, Edited by Eugene Braunwald, pp. 1184-1288.

Archer, Steffan et al., "Cell Reactions to Dielectrophoretic Manipulation," Mar. 1, 1999, Biochemical and Biophysical Research Communications, 1999 Academic Press, pp. 687-698.

Arentz, Thomas et al. "Incidence of pulmonary vein stenosis 2 years after radiofrequency catheter ablation of refractory atrial fibrillation." European Heart Journal. 2003. 24; pp. 963-969.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Augustyniak, Robert A. et al., "Sympathetic Overactivity as a Cause of Hypertension in Chronic Renal Failure," Aug. 14, 2001, Journal of Hypertension, 2002, vol. 20, 2002 Lippincott Williams & Wilkins, pp. 3-9.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg, 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, © 1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets the Long-Term Level of Renal Sympathetic Nerve Activity?," May 12, 2003, Integrative Physiology, Circulation Research 2003, vol. 92, © 2003 American Heart Association, pp. 1330-1336.

Bassett, C. Andrew L. et al., "Augmentation of Bone Reapair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, © 2004 IOP Publishing Ltd., pp. 1077-1093.

Berde, Charles and Gary R. Strichartz, "Local Anesthetics," Anesthesia, Chapter 13, 5th addition, Churchill-Livingston, Philadelphia 2000, pp. 491-521.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

Black, Henry R., M.D., "Resistant Hypertension 2004," presentation at Rush University Medical Center, Jul. 15, 2004, 40 pages.

Blad, B., et al., "An Electrical Impedance index to Assess Electroporation in Tissue," Tissue and Organ (Therapy) 2001, Oslo, pp. 31-34.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.

Bunch, Jared T. et al. "Mechanisms of Phrenic Nerve Injury During Radiofrequency Ablation at the Pulmonary Vein Orifice." Journal of Cardiovascular Electrophysiology. vol. 16, No. 12. pp. 1318-1325. Dec. 2005.

Burkhoff, Daniel. "Interventional Device-Based Therapy for CHF Will Redefine Current Treatment Paradigms". Columbia University. 2004. 32 slides.

Cahana, A. et al., "Acute Differential Modulation of Synaptic Transmission and Cell Survival During Exposure to Pulsed and Continuous Radiofrequency Energy," The Journal of Pain, May 2003, vol. 4, No. 4, © 2003 by the American Pain Society, pp. 197-202.

Cahana, Alex, M.D., "Pulsed Radiofrequency: A Neurobiologic and Clinical Reality," May 17, 2005, Anesthesiology 2005, vol. 103, No. 6, Dec. 2005, © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Campese, V.M. et al., "Renal Afferent Denervation Prevents the Progression of Renal Disease in the Renal Ablation Model of Chronic Renal Failure in the Rat," Jun. 13, 1995, American Journal of Kidney Diseases 1995, vol. 26, No. 5, 1995 the National Kidney Foundation, Inc., pp. 861-865.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Canbaz, Suat et al. "Electrophysiological evaluation of phrenic nerve injury during cardiac surgery—a prospective, controlled clinical study." BioMed Central. 5 pages. 2004.

Carls, G., et al., "Electrical and magnetic stimulation of the intercostal nerves: a comparative study," Electromyogr. din. Neurophysiol., vol. 37, 1997, pp. 509-512.

Carlson, Scott H. and J. Michael Wyss, "e-Hyertension, Opening New Vistas," Introductory Commentary, Hypertension 2000, vol. 35, American Heart Association, Inc., 2000, p. 538.

Carson, Peter. "Device-based Treatment for Chronic Heart Failure: Electrical Modulation of Myocardial Contractility". Transcatheter Cardiovascular Therapeutics 2005. 21 slides.

Chang, Donald C., "Cell poration and cell fusion using an oscillating electric field," Biophysical Journal, vol. 56, Oct. 1989, Biophysical Society, pp. 641-652.

Chiou, CW et al. "Efferent Vagal Innervation of the Canine Atria and Sinus and Atrioventricular Nodes". Circulation. Jun. 1997. 95(11):2573-2584. Abstract only. 2 pages.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Davalos, R. et al., "Electrical Impedance Tomography for Imaging Tissue Electroporation," Jul. 25, 2003, IEEE Transactions on Biomedical Engineering, vol. 51, No. 5, May 2004, IEEE 2004, pp. 761-767.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

DiBona, G., "Neural Control of the Kidney: Functionally Specific Renal Sympathetic Nerve Fibers," Starling Lecture, Am J Physiol Regulatory Integrative Comp Physiol 2000, 279, 2000 The American Physiological Society, pp. R1517-R1524.

Dibona, Gerald F., "Sympathetic Nervous System and the Kidney in Hypertension," Current Opinion in Nephrology and Hypertension 2002, vol. 11, 2002 Lippincott Williams & Wilkins, pp. 197-200.

Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.

Dibona, Gerald F. and Ulla C. Kopp, "Neural Control of Renal Function," Physiological Reviews Jan. 1997, vol. 77, No. 1, © 1997 American Physiological Society, pp. 75-197.

Dibona F., "Functionally Specific Renal Sympathetic Nerve Fibers: Role in Cardiovascular Regulation," Mar. 6, 2001, American Journal of Hypertension 2001, vol. 14, 2001 American Journal of Hypertension, Ltd. Published by Elsevier Science Inc., pp. 163S-170S.

Dibona, Gerald F., "Nervous Kidney—Interaction Between Renal Sympathetic Nerves and the Renin-Angiotensin System in the Control of Renal Function," Jun. 21, 2000, Hypertension 2000, vol. 36, 2000 American Heart Association, Inc., pp. 1083-1088.

Dibona, Gerald F., "Neural Control of the Kidney—Past, Present, and Future," Nov. 4, 2002, Novartis Lecture, Hypertension 2003, vol. 41, part 2, © 2002 American Heart Association, pp. 621-624.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dorros, Gerald, M.D., "Renal Artery Stenting State of the Art," presentation, TCT, Washington D.C., Sep. 2003, 27 pages.

Dueck, Ron, M.D., "Noninvasive Cardiac Output Monitoring," The Cardiopulmonary and Critical Care Journal, Chest, vol. 120, sec. 2, Aug. 2001, American College of Chest Physicians 2005, pp. 339-341, 5 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No. 15, 2 pages.

Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.

Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Delivery—Iontophoretic Balloon,," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 2000—A Rising Tide," May 18, 2004, © 2004 the American Heart Association, Hypertension Oct. 2004, pp. 1-7.

Fischell, Tim A. et al. "Ultrasonic Energy: Effects on Vascular Function and Integrity." Circulation: Journal of the American Heart Association. 1991. 84;pp. 1783-1795.

Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.

Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.

Fuster, Valentin et al. "ACC/AHA/ESC Practice Guidelines: ACA/ AHA/ESC 2006 Guidelines for the Management of Patients with Atrial Fibrillation." JACC vol. 48, No. 4, Aug. 15, 2006.

Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.

Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.

Gehl, Julie et al., "In vivo electroporation of skeletal muscle: threshold, efficacy and relation to electric field distribution," Biochimica et Biophysica Acta, 1428, 1999, Elsevier Science B.V. 1999, pp. 233-240.

Ghoname, El-sayed A. et al., "Percutaneous electrical nerve stimulation: an alternative to TENS in the management of sciatica," Apr. 26, 1999; Pain 1999, vol. 83, © 1999 International Association for the Study of Pain / Published by Elsevier Science B.V., pp. 193-199.

Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.

Goldberger, Jeffrey J. et al., "New technique for vagal nerve stimulation," Jun. 2, 1999, Journal of Neuroscience Methods 91, © 1999 Elsevier Science B.V., pp. 109-114.

Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pages (most of article in Russian language).

Greenwell, T.J. et al., "The outcome of renal denervation for managing loin pain haematuria syndrome," Oct. 30, 2003, Institute of Urology and Nephrology, London, UK, © 2004 BJU International, 4 pages.

Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.

Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.

Hammer, Leah W. "Differential Inhibition of Functional Dilation of Small Arterioles by Indomethacin and Glibenclamide." Hypertension. Feb. 2001 Part II. pp. 599-603.

Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.

Heida, Tjitske et al., "Investigating Membrane Breakdown of Neuronal Cells Exposed to Nonuniform Electric Fields by Finite-Element Modeling and Experiments," May 9, 2002. IEEE Transactions on Biomedical Engineering, vol. 49, No. 10, Oct. 2002, © 2002 IEEE, pp. 1195-1203.

Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.

Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.

Hopp, Francis A. and Jeanne L. Seagard, "Respiratory Responses to Selective Blockade of Carotid Sinus Baroreceptors in the Dog," Jun. 22, 2005, Am J Physiol Regul Integr Comp Physiol 1998, vol. 275, 2005 American Physiological Society, pp. R10-R18.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Norwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.

Huang, Wann-Chu et al. "Renal Denervation Prevents and Reverses Hyperinsulinemia-Induced Hypertension in Rats," Mar. 25, 1998, Hypertension 1998, vol. 32, 1998 American Heart Association, Inc., pp. 249-254.

Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.

Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.

International Search Report, PCT/US04/38498, Mailed Feb. 18, 2005, Applicant: G & L Consulting, LLC (3 pages).

Israili, Z.H., "Clinical pharmacokinetics of angiotensin II (AT) receptor blockers in hypertension," Journal of Human Hypertension 2000, Macmillan Publishers Ltd., vol. 14, pp. S73-S86.

Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.

Jia, Jianping and Pollock, Martin. "The pathogenesis of non-freezing cold nerve injury: Observations in the rat." Brain. 120; pp. 631-646. 1997.

Jia, Jianping et al. "Cold injury to nerves is not due to ischaemia alone." Brain. 121;pp. 989-1001. 1998.

Jin, Yuanzhe. et al. "Pulmonary Vein Stenosis and Remodeling After Electrical Isolation for Treatment of Atrial Fibrillation: Short- and Medium-Term Follow-Up." PACE, vol. 27. pp. 1362-1370. Oct. 2004.

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.

Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.

Joshi, R.P. et al., "Improved energy model for membrane electroporation in biological cells subjected to electical pulses," Apr. 9, 2002, Physical Review E, vol. 65, 041920-1, © 2002 The American Physical Society, 8 pages.

Joshi, R.P. et al., "Self-consistent simulations of elctroporation dynamics in biological cells subjected to ultrashort electrical pulses," Jun. 21, 2001, Physical Review E, vol. 64, 011913, © 2001The American Physical Society, pp. 1-10.

Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.

Kanduser, Masa et al., "Effect of surfactant polyoxyethylene glycol ($C_{12}E_8$) on electroporation of cell line DC3F," Aug. 20, 2002, Colloids and Surfaces A: Physiochem. Eng. Aspects 2003, vol. 214, © 2002 Elsevier Science B.V., pp. 205-217.

Katholi, Richard E., "Renal nerves in the pathogenesis of hypertension in experimental animals and humans," Am J Physiol., vol. 245, © 1983 the American Physiological Society, pp. F1-F14.

Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.

King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.

Kinney, Brian M., M.D., "High-Tech Healing—The evolution of therapeutic electromagnetic fields in plastic surgery," Plastic Surgery Products, Jun. 2004, pp. 32-36, 3 pages.

Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.

Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. pp. 250-254.

Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.

Kon, Valentina, "Neural Control of Renal Circulation," Miner Electrolyte Metab 1989, vol. 15, © 1989 S. Karger AG, pp. 33-43.

Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Kumagai, K. et al. "New Approach to Pulmonary Vein Isolation for Atrial Fibrillation Using a Multielectrode Basket Catheter". Circuation Journal. vol. 70, No. 1. Jan. 2006. Abstract only. 2 pages.

Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000, © 2000 National Kidney Foundation Inc., pp. 166-172.

Lavie, Peretz, Ph.D. and Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Michael A. (editor). SPORTSMed. Connecticut State Medical Society Committee on the Medical Aspects of Sports. Fall/Winter 2005. 10 pages.

Lee, Raphael C. and Jurgen Hannig, "Membrane Biology and Biophysics," Chapter 25, Surgical Research, © 2001 Academic Press, pp. 297-305.

Lee, Raphael C. et al., "Biophysical Injury Mechanisms in Electrical Shock Trauma," Annu. Rev. Biomed. Eng., 2000, vol. 02, Copyright © 2000 by Annual Reviews, pp. 477-509.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

Maeder, Micha, M.D. et al., "Contrast Nephropathy: Review Focusing on Prevention," Jun. 2, 2004, Journal of the American College of Cardiology Nov. 2, 2004, vol. 44, No. 9, © 2004 by the American College of Cardiology Foundation, pp. 1763-1771.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, Inc. 1999, 115 pages.

Medtronic, "SynchroMed Infusion System—Clinical Reference Guide for Pain Therapy," Medtronic, Inc. 1998, 198 pages.

Mehran, Roxana. "Renal insufficiency and contrast nephropathy: The most common, least understood risk factor". Cardiovascular Research Foundation. Columbia University Medical Center. 2005. 86 slides.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following A Single Ultrasound Pulse," Sep. 25, 1989, Ultrasound in Med.& Biol. 1990, vol. 16, No. 3, pp. 297-309.

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCl) injection, Rx only description, AstraZeneca 2001, 3 pages.

National Kidney Foundation, "Are You At Increased Risk for Chronic Kidney Disease?" © 2002 National Kidney Foundation, Inc., 14 pages.

Nelson, Lawrence D. and Jeffrey L. Osborn, "Neurogenic Control of Renal Function in Response to Graded Nonhypotensive Hemorrahage in Conscious Dogs," Sep. 13, 1992, Am. J. Physiol. 264, 1993, American Physiological Society 1993, pp. R661-R667.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Nozawa, Takashi et al., "Effects of Long Term Renal Sympathetic Denervation on Heart Failure After Myocardial Infarction in Rats," Sep. 22, 2001, Heart Vessels 2002, vol. 16, Springer-Verlag 2002, pp. 51-56.

Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005. pp. 546-554.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation." Abstract only. 1 page.

Pappone, Carlo and Santinelli, Vincenzo. "Multielectrode basket catheter: A new tool for curing atrial fibrillation?" Heart Rhythm, vol. 3, Issue 4, pp. 385-386. Apr. 2006.

Pappone, Carlo et al. "[2004][759] Pulmonary Vein Denervation Benefits Paroxysmal Atrial Fibrillation Patients after Circumferential Ablation." Abstract only. 1 page.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Podhajsky, R. J., et al. "The Histologic Effects of Pulsed and Continuous Radiofrequency Lesions at 42° C to Rat Dorsal Root Ganglion and Sciatic Nerve," SPINE, vol. 30, No. 9, 2005, Lippincott Williams & Wilkins Inc., pp. 1008-1013.

Pope, Jill. "Fixing a Hole: Treating Injury by Repairing Cells." Annals of the New York Academy of Sciences: Annals Extra. Jul. 6, 2006. 5 pages.

Popovic, Jennifer .R. and Margaret J. Hall,"1999 National Hospital Discharge Survey," Advance Data, No. 319, CDC, pp. 1-17 & 20.

Practice Guidelines Writing Committee and ESH/ESC Hypertension Guidelines Committee, "Practice Guidelines For Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Purerfellner, Helmut and Martinek, Martin. "Pulmonary vein stenosis following catheter ablation of atrial fibrillation." Current Opinion in Cardiology. 20; pp. 484-490. 2005.

Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Rump, L.C., "The Role of Sympathetic Nervous Activity in Chronic Renal Failure," J Clinical Basic Cardiology 2001, vol. 4, pp. 179-182.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.

Schauerte, P et al. "Catheter ablation of cardiac autonomic nerves for prevention of vagal atrial fibrillation." Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P et al. "Transvenous parasympathetic nerve stimulation in the inferior vena cava and atrioventricular conduction." Journal of Cardiovascular Electrophysiology. 11(1). Jan. 2000. Abstract only. 2 pages.

Scheiner, Avram, Ph.D., "The design, development and implementation of electrodes used for functional electrical stimulation," Thesis paper, Case Western Reserve University, May 1992, 220 pages.

Scherlag, BJ and Po, S. "The intrinsic cardiac nervous system and atrial fibrillation." Current Opinion in Cardiology. 21(1):51-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Shupak, Naomi M., "Therapeutic Uses of Pulsed Magnetic-Field Exposure: A Review," Radio Science Bulletin Dec. 2003, No. 307, pp. 9-32.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "The Role of Radiofrequency in Failed Back Surgery Patients," Current Review of Pain 2000, vol. 4, © 2000 by Current Science Inc., pp. 49-53.

Sobotka, Paul A. "Treatment Strategies for Fluid Overload, CHF Patients". CHF Solutions. Transcatheter Cardiovascular Therapeutics 2005. 20 slides.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Steffen, W. et al. "Catheter-delivered high intensity, low frequency ultrasound induces vasodilation in vivo." European Heart Journal. 1994. 15;pp. 369-376.

Steg, PG et al. "Pulsed ultraviolet laser irradiation produces endothelium-independent relaxation of vascular smooth muscle". Circulation: Journal of the American Heart Association. 1989. pp. 189-197.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002. pp. 184-189.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Thompson, Gregory. W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States,"

National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Shaohua et al., "Renal Injury Caused by Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.

Zundert, Jan Van, M.D. Fipp and Alex Cahana, M.D. Daapm, "Pulsed Radiofrequency in Chronic Pain Management: Looking for the Best Use of Electrical Current," Pain Practice 2005, vol. 5, Issue 2, © 2005 World Institute of Pain, pp. 74-76.

U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/688,178, Levin et al.
U.S. Appl. No. 11/940,922, filed Nov. 5, 2010, Gelfand et al.
U.S. Appl. No. 12/790,639, filed May 28, 2010, Wu et al.
U.S. Appl. No. 12/871,457, filed Aug. 30, 2010, Wu et al.
U.S. Appl. No. 13/007,370, filed Jan. 18, 2011, Gelfand et al.
U.S. Appl. No. 12/996,897, filed Dec. 13, 2010, Demarais.
U.S. Appl. No. 13/009,748, filed Jan. 19, 2011, Beetel et al.
U.S. Appl. No. 12/910,631, filed Oct. 22, 2010, Wu et al.

International Search Report and Written Opinion, PCT/US05/35693, Mailed on Mar. 8, 2006, Applicant: Ardian, Inc., 29 pages.
International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
International Search Report and Written Opinion for PCT/US2009/069334; Applicant: Ardian, Inc.; Mailing Date: Mar. 1, 2010, 10 pages.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Search Report; European Patent Application No. 09156661.2; Applicant: Ardian, Inc.; Date of Mailing: Jul. 23, 2009, 6 pages.

European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
European Search Report; European Patent Application No. 07868755.5; Applicant: Ardian, Inc.; Date of Mailing: Jul. 28, 2010, 7 pages.
Final Office Action; U.S. Appl. No. 11/233,814; Mailed on Jan. 29, 2009, 11 pgs.
Final Office Action; U.S. Appl. No. 11/266,993; Mailed on Jan. 18, 2010, 7 pgs.
Final Office Action; U.S. Appl. No. 11/363,867; Mailed on May 1, 2009, 8 pgs.
Final Office Action; U.S. Appl. No. 11/451,728; Mailed on Jan. 13, 2009, 7 pgs.
Final Office Action; U.S. Appl. No. 11/599,649; Mailed on Jan. 15, 2009, 10 pgs.
Final Office Action; U.S. Appl. No. 11/599,723; Mailed on Apr. 5, 2010, 17 pgs.
Non-Final Office Action; U.S. Appl. No. 10/408,665; Mailed on Mar. 21, 2006, 14 pgs.
Non-Final Office Action; U.S. Appl. No. 11/129,765; Mailed on May 18, 2007, 10 pgs.
Non-Final Office Action; U.S. Appl. No. 11/129,765; Mailed on Sep. 10, 2007, 5 pgs.
Non-Final Office Action; U.S. Appl. No. 11/129,765; Mailed on Oct. 6, 2006, 30 pgs.
Non-Final Office Action; U.S. Appl. No. 11/133,925; Mailed on Oct. 18, 2008, 41 pgs.
Non-Final Office Action; U.S. Appl. No. 11/144,173; Mailed on Apr. 5, 2007, 33 pgs.
Non-Final Office Action; U.S. Appl. No. 11/144,173; Mailed on Sep. 10, 2007, 5 pgs.
Non-Final Office Action; U.S. Appl. No. 11/144,298; Mailed Oct. 29, 2009, 8 pgs.
Non-Final Office Action; U.S. Appl. No. 11/144,298; Mailed on Apr. 5, 2007, 33 pgs.
Non-Final Office Action; U.S. Appl. No. 11/144,298; Mailed on Sep. 10, 2007, 5 pgs.
Non-Final Office Action; U.S. Appl. No. 11/144,298; Mailed on Dec. 29, 2008, 7 pgs.
Non-Final Office Action; U.S. Appl. No. 11/145,122; Mailed on Apr. 11, 2007, 33 pgs.
Non-Final Office Action; U.S. Appl. No. 11/145,122; Mailed on Sep. 10, 2007, 5 pgs.
Non-Final Office Action; U.S. Appl. No. 11/189,563; Mailed on May 28, 2009, 5 pgs.
Non-Final Office Action; U.S. Appl. No. 11/233,814; Mailed on Jun. 17, 2008, 12 pgs.
Non-Final Office Action; U.S. Appl. No. 11/252,462; Mailed on Feb. 22, 2010, 6 pgs.
Non-Final Office Action; U.S. Appl. No. 11/266,993; Mailed on Jul. 8, 2009, 5 pgs.
Non-Final Office Action; U.S. Appl. No. 11/266,993; Mailed on Dec. 30, 2008, 7 pgs.
Non-Final Office Action; U.S. Appl. No. 11/363,867; Mailed on Sep. 25, 2008, 10 pgs.
Non-Final Office Action; U.S. Appl. No. 11/368,553; Mailed on May 18, 2010, 4 pgs.
Non-Final Office Action; U.S. Appl. No. 11/368,553; Mailed on Oct. 7, 2009, 5 pgs.
Non-Final Office Action; U.S. Appl. No. 11/368,809; Mailed on Dec. 3, 2009, 4 pgs.
Non-Final Office Action; U.S. Appl. No. 11/368,949; Mailed on Jun. 11, 2010, 6 pgs.
Non-Final Office Action; U.S. Appl. No. 11/368,971; Mailed on Aug. 24, 2010, 9 pgs.
Non-Final Office Action; U.S. Appl. No. 11/451,728; Mailed on Jun. 12, 2008, 41 pgs.
Non-Final Office Action; U.S. Appl. No. 11/451,728; Mailed on Jul. 2, 2009, 5 pgs.
Non-Final Office Action; U.S. Appl. No. 11/451,728; Mailed on Dec. 28, 2009, 7 pgs.
Non-Final Office Action; U.S. Appl. No. 11/504,117; Mailed on Mar. 31, 2009, 10 pgs.
Non-Final Office Action; U.S. Appl. No. 11/599,649; Mailed on Mar. 30, 2009, 10 pgs.
Non-Final Office Action; U.S. Appl. No. 11/599,649; Mailed on Jun. 23, 2008, 9 pgs.
Non-Final Office Action; U.S. Appl. No. 11/599,723; Mailed on Jun. 26, 2009, 17 pgs.
Non-Final Office Action; U.S. Appl. No. 11/599,723; Mailed on Oct. 15, 2010, 16 pgs.
Non-Final Office Action; U.S. Appl. No. 11/599,882; Mailed on Jul. 6, 2009, 13 pgs.
Non-Final Office Action; U.S. Appl. No. 11/688,178; Mailed on Jun. 28, 2010, 5 pgs.
Non-Final Office Action; U.S. Appl. No. 11/840,142; Mailed on Apr. 3, 2009, 13 pgs.
Non-Final Office Action; U.S. Appl. No. 12/567,521; Mailed on Sep. 3, 2010, 9 pgs.
Non-Final Office Action; U.S. Appl. No. 12/616,708; Mailed Sep. 16, 2010, 10 pgs.
Non-Final Office Action; U.S. Appl. No. 12/725,375; Mailed on Oct. 12, 2010, 14 pgs.

* cited by examiner

METHODS AND APPARATUS FOR PERFORMING A NON-CONTINUOUS CIRCUMFERENTIAL TREATMENT OF A BODY LUMEN

REFERENCE TO RELATED APPLICATION

The present application is a continuation-in-part application of each of the following co-pending United States patent application:

(1) U.S. patent application Ser. No. 11/129,765, filed May 13, 2005, which (a) claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/408,665, filed Apr. 8, 2003, which claims the benefit of U.S. Provisional Application Nos. 60/370,190 filed Apr. 8, 2002; 60/415,575, filed Oct. 3, 2002; and 60/442,970, filed Jan. 29, 2003.

(2) U.S. patent application Ser. No. 11/189,563 filed Jul. 25, 2005, which (a) is a continuation-in-part of U.S. patent application Ser. No. 11/129,765, filed May 13, 2005, which claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/900,199, filed Jul. 28, 2004 (now U.S. Pat No. 6,978,174), which is a continuation-in-part of U.S. patent application Ser. No. 10/408,665, filed Apr. 8, 2003, which claims the benefit of U.S. Provisional Application Nos. 60/370,190 filed Apr. 8, 2002; 60/415,575, filed Oct. 3, 2002; and 60/442,970, filed Jan. 29, 2003.

All the foregoing applications and patent are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for performing a non-continuous circumferential treatment of a body lumen. Several embodiments of such methods and apparatus are directed to circumferential treatments of the body lumen that apply energy in one or more discrete treatment areas to form one or more lesions that are not contiguous or continuous about any complete circumference of a cross-section normal to a longitudinal axis of the body lumen.

BACKGROUND

Applicants have described methods and apparatus for treating a variety of renal and cardio-renal diseases, such as heart failure, renal disease, renal failure, hypertension, contrast nephropathy, arrhythmia and myocardial infarction, by modulating neural fibers that contribute to renal function, e.g., denervating tissue containing the neural fibers that contribute to renal function. This is expected to reduce renal sympathetic nervous activity, which increases removal of water and sodium from the body, and returns renin secretion to more normal levels. Normalized renin secretion causes blood vessels supplying the kidneys to assume a steady state level of dilation/constriction, which provides adequate renal blood flow. See, for example, Applicants' co-pending U.S. patent application Ser. Nos.: (a) Ser. No. 10/408,665, filed Apr. 8, 2003; (b) Ser. No. 11/129,765, filed on May 13, 2005; (c) Ser. No. 11/189,563, filed on Jul. 25, 2005; (d) Ser. No. 11/363,867, filed on Feb. 27, 2006; (e) Ser. No. 11/504,117, filed on Aug. 14, 2006; as well as U.S. Pat. No. 6,978,174. All of these applications and the patent are incorporated herein by reference in their entireties.

Applicants also have previously described methods and apparatus for intravascularly-induced neuromodulation or denervation of an innervated blood vessel in a patient or any target neural fibers in proximity to a blood vessel, for example, to treat any neurological disorder or other medical condition. Nerves in proximity to a blood vessel may innervate an effector organ or tissue. Intravascularly-induced neuromodulation or denervation may be utilized to treat a host of neurological disorders or other medical conditions, including, but not limited to, the aforementioned conditions including heart failure and hypertension, as well as pain and peripheral arterial occlusive disease (e.g., via pain mitigation). The methods and apparatus may be used to modulate efferent or afferent nerve signals, as well as combinations of efferent and afferent nerve signals. See, for example, Applicants' co-pending U.S. patent application Ser. No. 11/599,649, filed on Nov. 14, 2006, entitled Methods and Apparatus for Intravascularly-Induced Neuromodulation or Denervation, which is incorporated herein by reference in its entirety.

Although the foregoing methods are useful by themselves, one challenge of neuromodulation and/or denervation is sufficiently affecting the neural tissue from within the vessel. For example, intravascular neuromodulation should avoid increasing the risk of acute and/or late stenosis. Therefore, it would be desirable to provide methods and apparatus that further address these challenges.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

Figure 1:
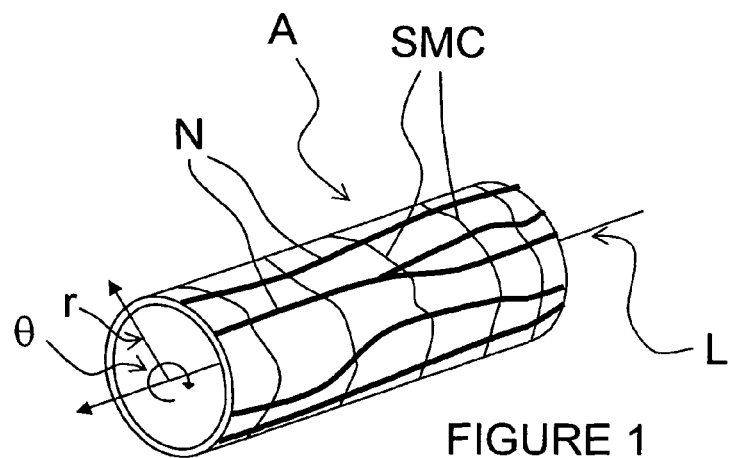
FIG. 1 is a schematic isometric detail view showing a common location of neural fibers proximate an artery.

The applicants have discovered that it may be desirable to perform a circumferential treatment of a body lumen to positively affect a medical condition by applying energy to discrete zones that are non-continuous along the complete circumference of a radial cross-section generally normal to the lumen wall. For example, in the treatment of atrial fibrillation or other arrhythmia, a circumferential treatment may be achieved by forming a continuous circumferential lesion that is continuous completely about a normal cross-section of the pulmonary vein to disrupt aberrant electrical signals. In the treatment of heart failure, a circumferential treatment may be achieved by forming a similar continuous circumferential lesion that is continuous completely about a normal cross-section of a renal artery to reduce renal sympathetic neural activity. However, continuous circumferential lesions that extend continuously about a full 360° of the circumference of a cross-section normal to the body lumen or tissue in proximity to the body lumen may increase a risk of acute and/or late stenosis formation within the blood vessel. Therefore, many of the embodiments described below are directed to forming discrete, non-continuous lesions normal of a lumen without adversely affecting the vessel.

Such non-continuous treatments may, for example, be conducted from an intravascular or intraluminal position, which can include treatment utilizing elements passed from an intravascular location to an extravascular location, i.e., intra-to-extravascular treatment. However, it should be understood that extravascular treatment apparatus and methods in accordance with the present invention also may be provided.

The treatments can be applied relative to nerves, including nervous tissue in the brain, or other target structures within or in proximity to a blood vessel or other body lumen that travel at least generally parallel or along a lengthwise dimension of the blood vessel (body lumen). The target structures can additionally or alternatively comprise a rotational orientation relative to the blood vessel (body lumen). Several disclosed embodiments of non-continuous circumferential treatments may reduce the risk of acute and/or late stenosis formation by treating neural matter along portions of multiple radial planes or cross-sections that are normal to, and spaced apart along, the lengthwise or longitudinal axis of the blood vessel (body lumen).

The treatment area at each radial plane or cross-section defines a treatment zone that is not completely continuous along a normal circumference, i.e., defines a treatment zone without a continuous circumferential lesion normal to the longitudinal axis. However, superimposition of the multiple treatment zones along the multiple radial planes or normal cross-sections defines a non-continuous, overlapping circumferential treatment zone along a lengthwise or longitudinal segment of the blood vessel (body lumen). In some embodiments, this overlapping treatment zone may provide a non-continuous, but substantially fully circumferential treatment without formation of a continuous circumferential lesion normal to the vessel (lumen). In other embodiments, the overlapping treatment zone may provide a non-continuous, partial circumferential treatment.

In this manner, a non-continuous circumferential treatment is performed over a lengthwise segment of the blood vessel (body lumen), as compared to a continuous circumferential treatment at a single normal cross-section or radial plane. Target structures substantially traveling along the lengthwise dimension of the blood vessel (body lumen) are thus circumferentially affected in a non-continuous fashion without formation of the continuous circumferential lesion along any normal cross-section or radial plane of the blood vessel (body lumen). This may reduce a risk of acute or late stenosis formation within the blood vessel (body lumen). A non-continuous circumferential treatment can thus comprise a treatment conducted at multiple positions about the lengthwise dimension of a body lumen, wherein the treatment zone at any one lengthwise position does not comprise a continuous circumferential lesion completely about a radial plane or normal cross-section, but wherein a superimposition of the treatment zones at all or some of the lengthwise positions may define an overlapping circumferential treatment zone.

The non-continuous circumferential treatment optionally may be achieved via apparatus positioned within a body lumen in proximity to target neural fibers for application of energy to the target neural fibers. The treatment may be induced, for example, via electrical and/or magnetic energy application, via thermal energy application (either heating or cooling), via mechanical energy application, via chemical energy application, via nuclear or radiation energy application, via fluid energy application, etc. Such treatment may be achieved, for example, via a thermal or non-thermal electric field, via a continuous or pulsed electric field, via a stimulation electric field, via localized drug delivery, via high intensity focused ultrasound, via thermal techniques, via athermal techniques, combinations thereof, etc. Such treatment may, for example, effectuate irreversible electroporation or electrofusion, necrosis and/or inducement of apoptosis, alteration of gene expression, action potential blockade or attenuation, changes in cytokine up-regulation, ablation and other conditions in target neural fibers. All or a part of the apparatus optionally may be passed through a wall of the body lumen to an extraluminal location in order to facilitate the treatment. The body lumen may, for example, comprise a blood vessel, and the apparatus may be positioned within the blood vessel via well-known percutaneous techniques.

Treatment may be achieved via either direct alteration of the target structures (e.g., target neural structures) or at least in part via alteration of the vascular or other structures that support the target structures or surrounding tissue, such as arteries, arterioles, capillaries, veins or venules. In some embodiments, the treatment may be achieved via direct application of energy to the target or support structures. In other embodiments, the treatment may be achieved via indirect generation and/or application of the energy, such as through application of an electric field or of high-intensity focused ultrasound that causes resistive heating in the target or supporting structures. Alternative thermal techniques also may be utilized.

In some embodiments, methods and apparatus for real-time monitoring of the treatment and its effects on the target or support structures, and/or in non-target tissue, may be provided. Likewise, real-time monitoring of the energy delivery apparatus may be provided. Power or total energy delivered, impedance and/or the temperature, or other characteristics of the target or the non-target tissue, or of the apparatus, additionally or alternatively may be monitored.

When utilizing an electric field to achieve desired circumferential treatment, the electric field parameters may be altered and combined in any combination, as desired. Such parameters can include, but are not limited to, frequency, voltage, power, field strength, pulse width, pulse duration, the shape of the pulse, the number of pulses and/or the interval between pulses (e.g., duty cycle), etc. For example, suitable field strengths can be up to about 10,000 V/cm, and may be either continuous or pulsed. Suitable shapes of the electrical waveform include, for example, AC waveforms, sinusoidal waves, cosine waves, combinations of sine and cosine waves, DC waveforms, DC-shifted AC waveforms, RF waveforms, microwaves, ultrasound, square waves, trapezoidal waves, exponentially-decaying waves, and combinations thereof.

When utilizing a pulsed electric field, suitable pulse widths can be of any desired interval, for example, up to about 1 second. The field includes at least one pulse, and in many applications the field includes a plurality of pulses or is continuously applied, e.g., for up to several minutes. Suitable pulse intervals include, for example, intervals less than about 10 seconds. These parameters are provided as suitable examples and in no way should be considered limiting.

When utilizing thermal mechanisms to achieve the desired treatment, protective elements optionally may be provided to protect the non-target tissue, such as the smooth muscle cells, from thermal damage during the thermally-induced non-continuous circumferential treatment. For example, when heating target nerves or support structures, protective cooling elements, such as convective cooling elements, may be provided to protect the non-target tissue. Likewise, when cooling target nerves or support structures, protective heating elements, such as convective heating elements, may be utilized to protect the non-target tissue. Thermal energy may be applied either directly or indirectly for a brief or a sustained period of time in order to achieve, for example, desired neuromodulation or denervation. Feedback, such as sensed temperature and/or impedance, along target or non-target tissue or along the apparatus, optionally may be used to control and monitor delivery of the thermal energy.

The non-target tissue optionally may be protected during, e.g., the neuromodulation or denervation, by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal (or other) energy on the target or support structures, such that an intensity of the energy is insufficient to induce thermal damage in the non-target tissue distant from the target or support structures.

Additional and alternative methods and apparatus may be utilized to achieve a non-continuous circumferential treatment without formation of a continuous circumferential lesion, as described hereinafter. To better understand the structures of devices of the present invention and the methods of using such devices for non-continuous circumferential treatment, it is instructive to examine a common neurovascular anatomy in humans.

B. Neurovascular Anatomy Summary

FIG. 1 illustrates a common anatomical arrangement of neural structures relative to body lumens or vascular structures, typically arteries. Neural fibers N generally may extend longitudinally along the lengthwise dimension L of an artery A about a relatively small range of positions along the radial dimension r, often within the adventitia of the artery. The artery A has smooth muscle cells SMC that surround the arterial circumference and generally spiral around the angular dimension θ of the artery, also within a relatively small range of positions along the radial dimension r. The smooth muscle cells of the artery accordingly have a lengthwise or longer dimension generally extending transverse (i.e., non-parallel) to the lengthwise dimension of the blood vessel. The misalignment of the lengthwise dimensions of the neural fibers and the smooth muscle cells is defined as "cellular misalignment."

The cellular misalignment of the nerves N and the smooth muscle cells SMC may be exploited to selectively affect the nerve cells with reduced effect on the smooth muscle cells. More specifically, a non-continuous circumferential treatment may be achieved by superimposing treatments undertaken along multiple radial or cross-sectional planes of the artery A that are separated along the lengthwise dimension L of the artery, rather than performing a continuous circumferential treatment along a single radial plane or cross-section of the artery. In this manner, due to the cellular misalignment, the lengthwise-oriented neural fibers may experience a full, non-continuous circumferential treatment, while the angularly-oriented smooth muscle cells may experience only a partial circumferential treatment. Monitoring elements optionally may be utilized to assess an extent of treatment induced in the nerves and/or in the smooth muscle cells, as well as to adjust treatment parameters to achieve a desired effect.

C. Embodiments of Apparatus and Methods for Non-continuous Circumferential Treatment of a Body Lumen FIGS. 2-7 and 9 illustrate examples of intravascular systems and methods for performing non-continuous circumferential treatments. The applicants have described intravascular and intra-to-extravascular systems for neuromodulation or denervation, for example, in co-pending U.S. patent application Ser. No. 11/129,765, filed May 13, 2005; and Ser. No. 11/363,867, filed on Feb. 27, 2006, both of which have been incorporated herein by reference. The applicants also have described extravascular systems for neuromodulation or denervation (see, for example, U.S. patent application Ser. No. 11/189,563, filed Jul. 25, 2005, incorporated herein by reference), and it should be understood that non-continuous circumferential treatments may be performed using extravascular (or extraluminal) systems, in addition to intravascular (intraluminal) or intra-to-extravascular (intra-to-extraluminal) systems (see FIGS. 10A and 10B). Applicants also have previously described thermal systems for neuromodulation or denervation, for example, in co-pending U.S. patent application Ser. No. 11/504,117, filed on Aug. 14, 2006.

Referring now to FIGS. 2A-2J, the embodiment of an apparatus 300 comprises a catheter 302 having an optional positioning element 304 (e.g., a balloon, an expandable wire basket, other mechanical expanders, etc.) and expandable electrode element 306 positioned along the shaft of the catheter and illustratively located over the positioning element. The electrode element 306 can have one or more electrodes 307 electrically coupled to a field generator 50 for delivery of an electric field to the target neural fibers. In an alternative embodiment, one or more of the electrode(s) 307 of the electrode element 306 may comprise Peltier electrodes for heating or cooling the target neural fibers to modulate the fibers. The electrode(s) 307 optionally may be individually assignable and may be utilized in a bipolar fashion, and/or may be utilized in a monopolar fashion with an external ground pad attached to the exterior of the patient.

The field generator 50, as well as any of the electrode embodiments described herein, may be utilized with any embodiment of the present invention for delivery of an electric field with desired field parameters. The field generator 50 can be external to the patient. It should be understood that electrodes of embodiments described hereinafter may be electrically connected to the generator even though the generator is not explicitly shown or described with each embodiment. Furthermore, the field generator optionally may be positioned internal to the patient, and the electrodes and/or the field generator optionally may be temporarily or permanently implanted within the patient.

The positioning element 304 optionally may position or otherwise drive the electrode(s) 307 into contact with the vessel wall. The positioning element 304 may also comprise an impedance-altering element that alters the impedance within the vessel during the therapy to direct the electric field across the vessel wall. This may reduce an energy required to achieve desired neuromodulation or denervation and may reduce a risk of injury to non-target tissue. Applicants have previously described use of an impedance-altering element, for example, in co-pending U.S. patent application Ser. No. 11/266,993, filed Nov. 4, 2005, which is incorporated herein by reference in its entirety. When the positioning element 304 comprises an inflatable balloon, as in FIGS. 2A-J, the balloon may serve as both a centering and/or expansion element for the expandable electrode element 306, and as an impedance-altering electrical insulator for directing an electric field delivered via the electrode(s) 307 into or across the vessel wall for modulation of target neural fibers. Electrical insulation provided by the element 304 may reduce the magnitude of applied energy or other parameters of the electric field necessary to achieve desired modulation of the target fibers, up to and including full denervation of tissue containing the target fibers.

Furthermore, element 304 optionally may be utilized as a thermal element. For example, it may be inflated with a chilled fluid that serves as a heat sink for removing heat from tissue that contacts the element. Conversely, element 304 may be inflated with a warmed fluid that heats tissue in contact with the element. The thermal fluid within the element optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below.

The electrode(s) 307 can be individual electrodes (i.e., independent contacts), a segmented electrode with commonly connected contacts, or a single continuous electrode. Furthermore, the electrode(s) 307 may be configured to provide a bipolar signal, or the electrode(s) 307 may be used together or individually in conjunction with a separate patient ground pad for monopolar use. As an alternative or in addition to placement of the electrode(s) 307 along the expandable electrode element 306, as in FIGS. 2, the electrode(s) 307 may be attached to the positioning element 304 such that they contact the wall of the artery upon expansion of the positioning element. In such a variation, the electrode(s) may, for example, be affixed to the inside surface, outside surface or at least partially embedded within the wall of the positioning element (see FIGS. 5A and 5B). In another embodiment, the electrode(s) do not contact the vessel wall, and may be positioned at any desired location within the vessel.

The electrode(s) 307 or any other portion of the apparatus 300, such as catheter 302 or element 304, additionally or alternatively may comprise one or more sensors, such as thermocouples 310, for monitoring the temperature or other parameters of the target tissue, the non-target tissue, the electrodes, the positioning element and/or any other portion of the apparatus 300 or of the patient's anatomy. The treatment regime may be controlled using the measured parameter(s) as feedback. This feedback may be used, for example, to maintain the parameter(s) below a desired threshold, for example, a threshold that may cause injury to the non-target tissues. Conversely, the feedback may be used to maintain the parameter(s) at or above a desired threshold, for example, a threshold that may induce a desired effect in the target tissues, such as neuromodulation of target neural fibers or denervation of tissues innervated by the target neural fibers. Furthermore, the feedback may be used to keep the parameter(s) within a range that will induce the desired effect in the target tissues without injuring the non-target tissues to an unacceptable extent. Multiple parameters (or the same or multiple parameters at multiple locations) optionally may be used as control feedback for ensuring the desired effects while mitigating the undesired effects.

Figure 2A:
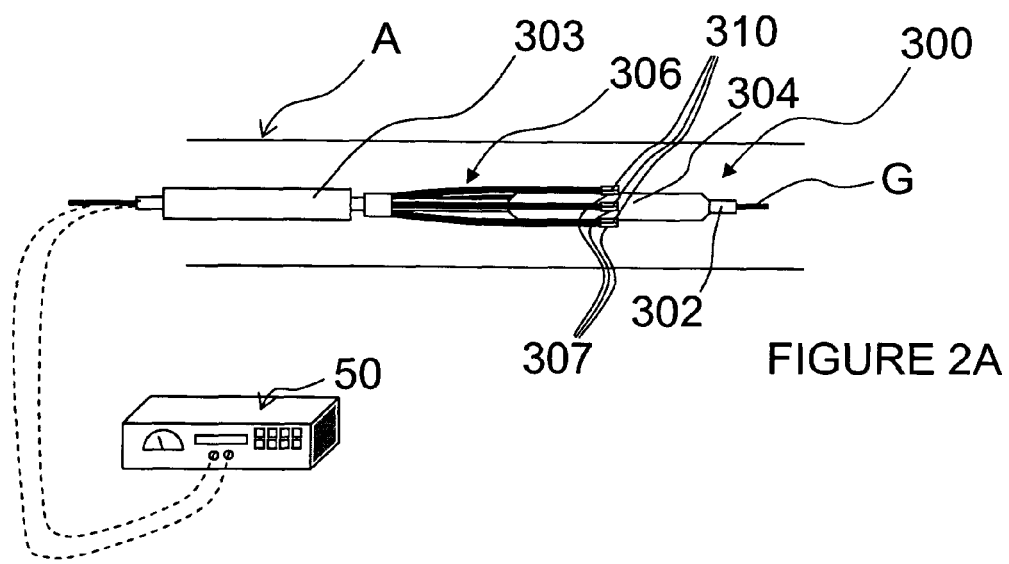
FIGS. 2A-2J are schematic side views, partially in section, and cross-sectional views illustrating an example of methods and apparatus for a non-continuous circumferential treatment of a body lumen.

As seen in FIG. 2A, the catheter 302 may be delivered to a treatment site within the artery A (or within a vein or any other vessel in proximity to target neural fibers) in a low profile delivery configuration, for example, through the guide catheter or sheath 303. Alternatively, catheters may be positioned in multiple vessels for neuromodulation, e.g., within both an artery and a vein. Multi-vessel techniques for electric field neuromodulation have been described previously, for example, in Applicant's co-pending U.S. patent application Ser. No. 11/451,728, filed Jul. 12, 2006, which is incorporated herein by reference in its entirety.

Figure 2B:
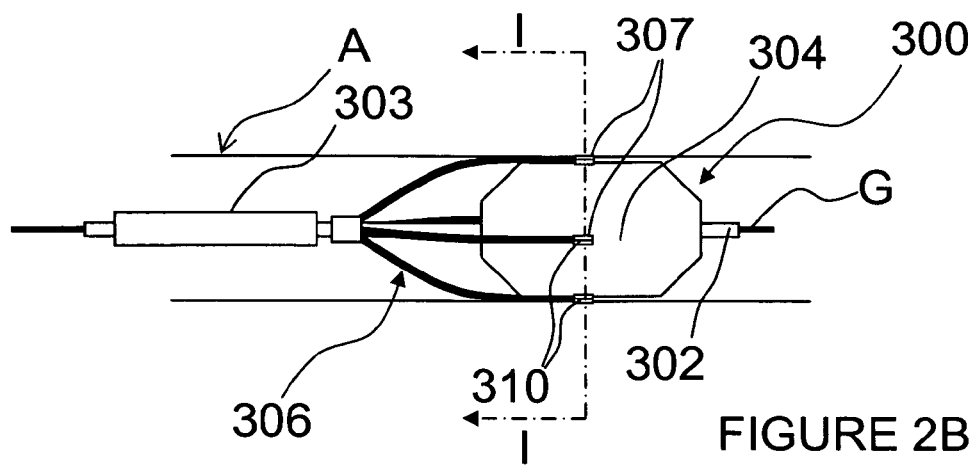

Once positioned within the vasculature as desired, the optional positioning element 304 may be expanded to deploy the electrode element 306 and bring the electrode(s) 307 into contact with an interior wall of the vessel, as seen in FIG. 2B. An electric field then may be generated by the field generator 50, transferred through the catheter 302 to the electrode element 306 and the electrodes 307, and delivered via the electrode(s) 307 across the wall of the artery. The electric field modulates the activity along neural fibers within the wall of the artery or in proximity to the artery, e.g., at least partially denervates tissue or organ(s) innervated by the neural fibers. This may be achieved, for example, via ablation or necrosis or via non-ablative injury or other changes to the target neural fibers or supporting structures. The electric field also may induce electroporation in the neural fibers.

Figure 2C:
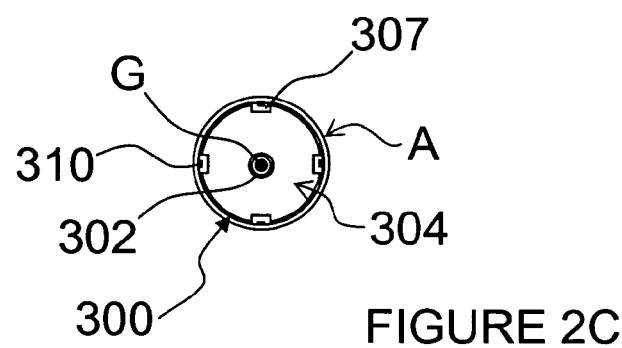
Figure 2D:
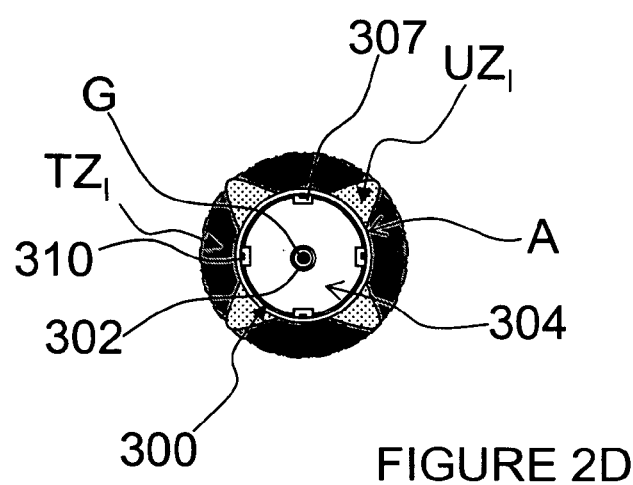

As seen in the cross-sectional view of FIG. 2C taken along the radial plane I-I of FIG. 2B, the apparatus 300 illustratively comprises four electrodes 307 equally spaced about the circumference of the electrode element 306 and the positioning element 304. As seen in FIG. 2D, when utilized in a monopolar fashion in combination with an external ground (not shown; per se known), the circumferential segments treated by each electrode overlap to form discrete treatment zones $TZ_I$ that are not continuous completely around the circumference of the artery in a radial plane normal to the vessel wall. As a result, there are discrete untreated zones $UZ_I$ about the circumference of the artery.

Figure 2E:
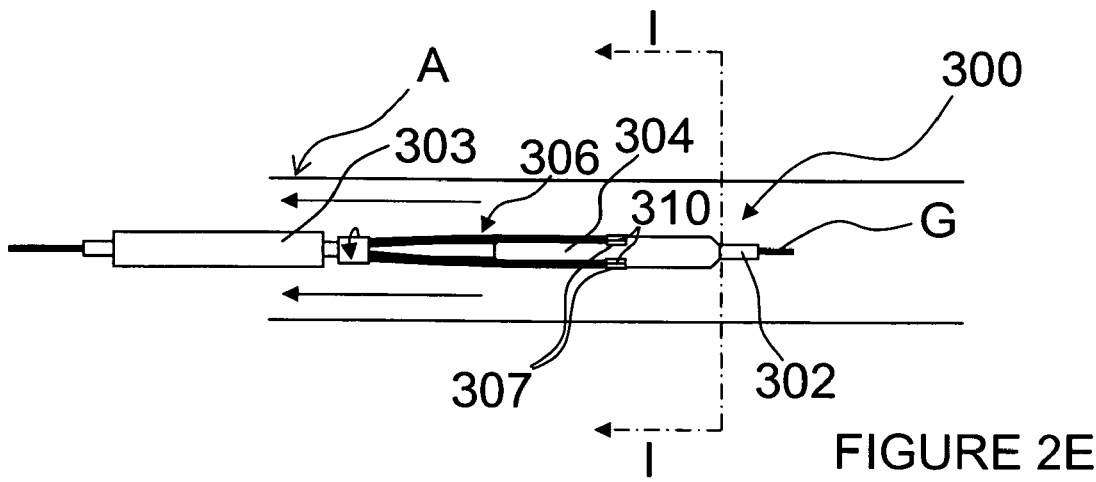

As seen in FIG. 2E, the electrode element 306 may be collapsed about the radial dimension r of the artery such that the electrodes 307 do not contact the vessel wall, e.g., by collapsing the positioning element 304. The electrode element 306 may be rotated about the angular dimension θ of the artery to angularly reposition the electrodes 307 (best shown in FIG. 2G). This rotation may be achieved, for example, by angularly rotating the catheter 302. In FIG. 2E, the electrode element illustratively has been rotated approximately 45° about the angular dimension of the artery. In the embodiment of apparatus 300 shown in FIGS. 2A-G, the electrodes are equally spaced about the circumference of the apparatus such that a 45° angular rotation repositions the electrodes approximately halfway between the initial positions of the electrodes shown in FIG. 2D.

Figure 2F:
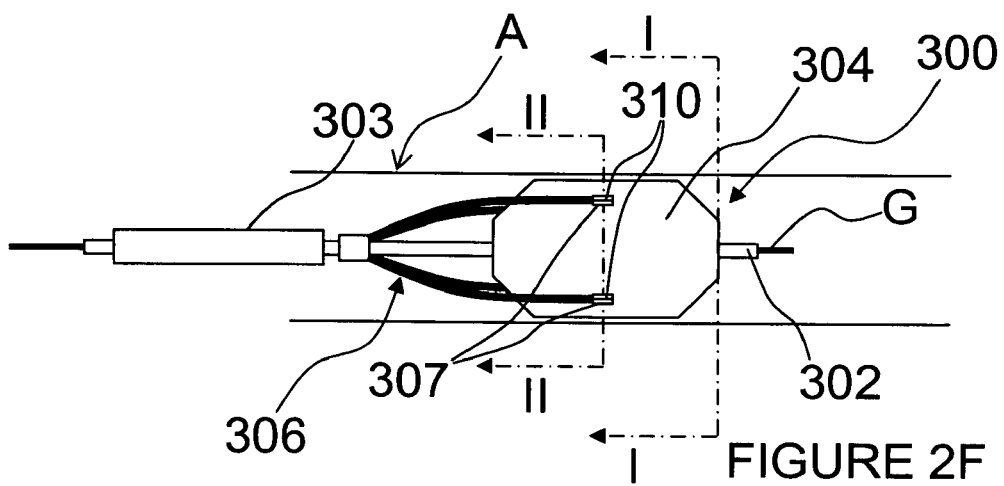

In addition to angular repositioning of the electrodes, the electrodes may be repositioned along the lengthwise or longitudinal dimension L of the artery, which is also shown in FIG. 2E as the longitudinal offset between the electrodes 307 and the radial plane I-I. Such lengthwise repositioning may occur before, after or concurrent with angular repositioning of the electrodes. As seen in FIG. 2F, once repositioned in both the lengthwise and angular dimensions, the electrode element 306 may be re-expanded about the radial dimension to contact the electrodes 307 with the vessel wall. An electric field then may be delivered via the angularly and lengthwise repositioned electrodes 307 along the normal radial plane II-II.

Figure 2G:
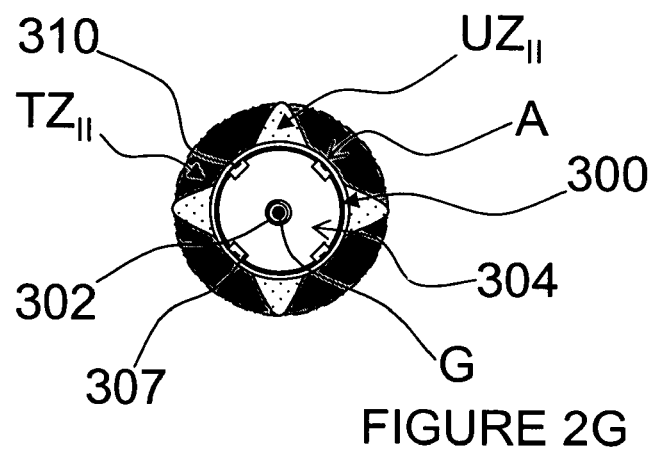
Figures 2H, 2I:
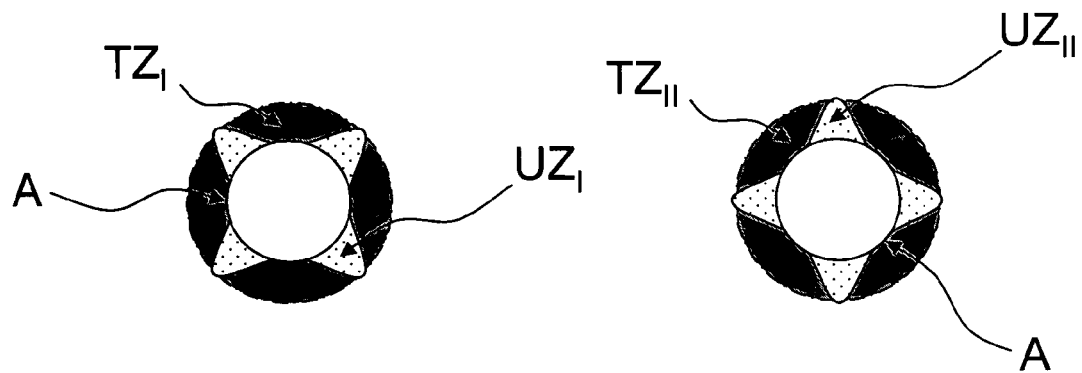

In FIG. 2G, the treatment along the radial plane II-II of FIG. 2F creates treatment zone $TZ_{II}$, and untreated zone $UZ_{II}$. As with the treatment zone $TZ_I$ of FIG. 2D, the treatment zone $TZ_{II}$, of FIG. 2G is not continuous about the complete circumference of the artery. FIGS. 2H and 2I allow comparison of the treatment zone $TZ_I$ and the treatment zone $TZ_{II}$. The apparatus 300 is not shown in FIGS. 2H and 2I, e.g., the apparatus may have been removed from the patient to complete the procedure.

Figure 2J:
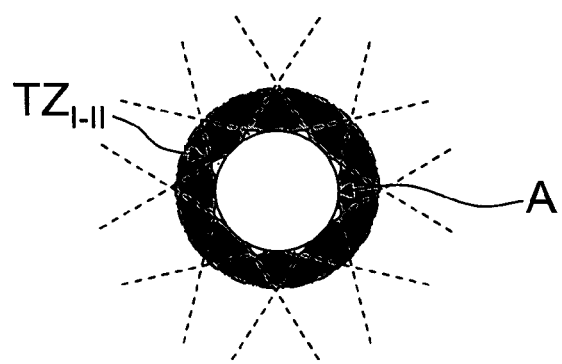

As shown, the untreated zones $UZ_I$ and $UZ_{II}$ along the radial planes I-I and II-II, respectively, are angularly offset from one another about the angular dimension θ of the artery (see FIG. 1). As seen in FIG. 2J, by superimposing the treatment zones $TZ_I$ and $TZ_{II}$, which are positioned along different cross-sections or radial planes of the artery A, a composite treatment zone $TZ_{I-II}$ is formed that provides a non-continuous, yet substantially circumferential treatment over a lengthwise segment of the artery. This superimposed treatment zone beneficially does not create a continuous circumferential lesion along any individual radial plane or cross-section normal to the artery, which may reduce a risk of acute or late stenosis formation, as compared to previous circumferential treatments that create a continuous circumferential lesion.

As discussed previously, non-continuous circumferential treatment by positioning electrodes at different angular orientations along multiple lengthwise locations may preferentially affect anatomical structures that substantially propagate along the lengthwise dimension of the artery. Such anatomical structures can be neural fibers and/or structures that support the neural fibers. Furthermore, such a non-continuous circumferential treatment may mitigate or reduce potentially undesirable effects induced in structures that propagate about the angular dimension of the artery, such as smooth muscle cells. The angular or circumferential orientation of the smooth muscle cells relative to the artery may at least partially explain why continuous circumferential lesions may increase a risk of acute or late stenosis.

Although in FIGS. 2A-J the electrode element 306 is expanded via the positioning element 304, it should be understood that expandable electrode elements or electrodes in accordance with the present invention additionally or alternatively may be configured to self-expand into contact with the vessel wall. For example, the electrodes may self-expand after removal of a sheath or a guide catheter 303 constraining the electrodes in a reduced delivery configuration. The electrodes or electrode elements may, for example, be fabricated from (or coupled to) shape-memory elements that are configured to self-expand. Self-expanding embodiments optionally may be collapsed for retrieval from the patient by re-positioning of a constraining sheath or catheter over the self-expanding elements. Optionally, the electrode element may be shapeable by a medical practitioner, e.g., in order to provide a desired wall-contacting profile.

Figure 3:
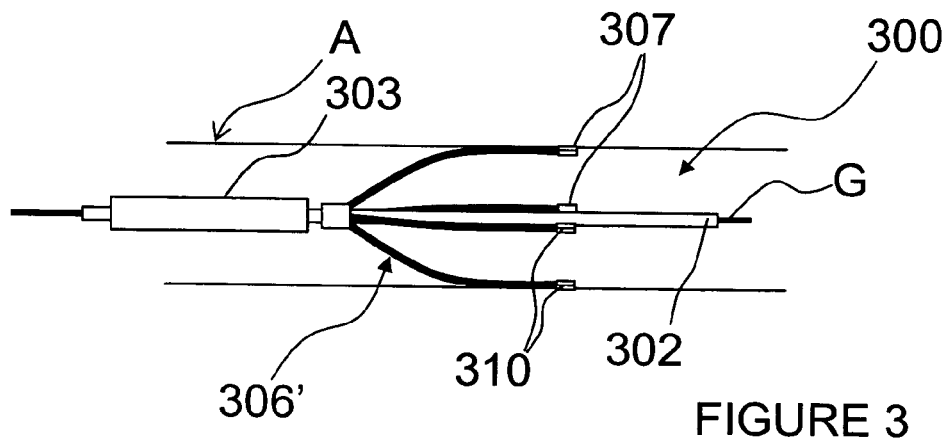
FIG. 3 is a schematic side view, partially in section, illustrating an alternative embodiment of the methods and apparatus of FIGS. 2.

FIG. 3 illustrates an alternative embodiment of the apparatus 300 having a self-expanding electrode element 306'. Positioning element 304 has been removed from the apparatus. In use, the apparatus 300 is advanced to a treatment site within sheath or guide catheter 303. The sheath is removed, and the element 306' self-expands to bring the electrodes 307 into contact with the vessel wall. Advantageously, blood continues to flow through the artery A during formation of treatment zone $TZ_I$. The element 306' then may be partially or completely collapsed (e.g., within sheath 303), angularly rotated relative to the vessel, laterally repositioned relative to the vessel, and re-expanded into contact with the vessel wall along a different radial plane or cross-section. Treatment may proceed at the new location and in the new angularly orientation in the presence of blood flow, e.g., to form overlapping treatment zone $TZ_{II}$ that completes a non-continuous circumferential treatment zone $TZ_{I-II}$ when superimposed with the treatment zone $TZ_I$. The element 306' then may be re-collapsed, and the apparatus 300 may be removed from the patient to complete the procedure.

Figure 4:
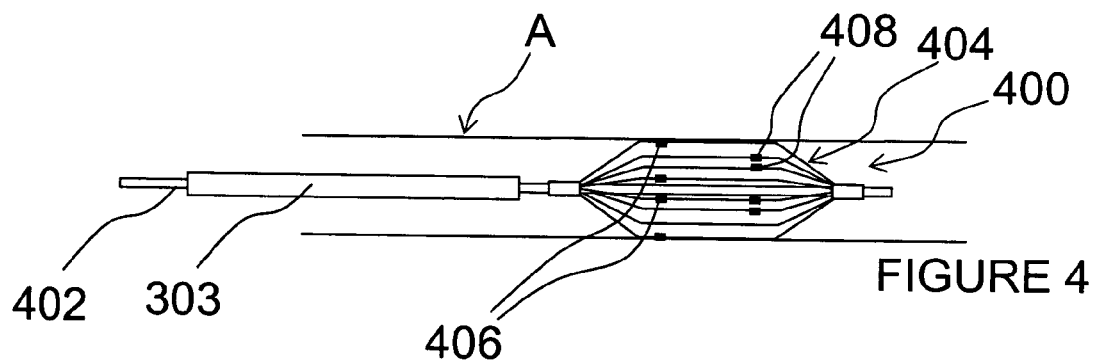
FIG. 4 is a schematic side view, partially in section, illustrating further alternative methods and apparatus for non-continuous circumferential treatments.

Referring now to FIG. 4, it may be desirable to achieve a non-continuous circumferential treatment without angular and/or lengthwise repositioning of electrodes or other energy delivery elements. To this end, in another embodiment an apparatus 400 comprises catheter 402 having actively-expandable or self-expanding basket 404 having proximal electrodes 406 and distal electrodes 408 spaced longitudinally apart from the proximal electrodes. The proximal electrodes 406 and distal electrodes 408 are also spaced apart radially about the basket and electrically coupled to the field generator 50 (see FIG. 2A). The proximal electrodes 406 can be positioned along different struts or elements of the basket than the distal electrodes. The proximal and distal electrodes are accordingly angularly and laterally offset from one another.

The proximal electrodes may be operated independently of the distal electrodes, and/or the proximal and distal electrodes all may be operated at the same polarity, e.g., in a monopolar fashion as active electrodes in combination with an external ground. Alternatively or additionally, the proximal electrodes may be utilized in a bipolar fashion with one another and/or the distal electrodes may be utilized in a bipolar fashion with one another. The proximal and distal electrodes preferably are not utilized together in a bipolar fashion. By treating with the distal electrodes 408, the treatment zone $TZ_I$ of FIG. 2H may be formed about the artery. Treating with the proximal electrodes 406 may create the treatment zone $TZ_{II}$ of FIG. 2I, which is angularly offset relative to the treatment zone $TZ_I$. Superimposition of the treatment zones $TZ_I$ and $TZ_{II}$ creates the non-continuous circumferential treatment zone $TZ_{I-II}$ over a lengthwise segment of the artery.

The proximal and distal electrodes optionally may be utilized concurrently to concurrently form the treatment zones $TZ_I$ and $TZ_{II}$. Alternatively, the electrodes may be operated sequentially in any desired order to sequentially form the treatment zones. As yet another alternative, the treatment zones may be formed partially via concurrent treatment and partially via sequential treatment.

Figure 5A:
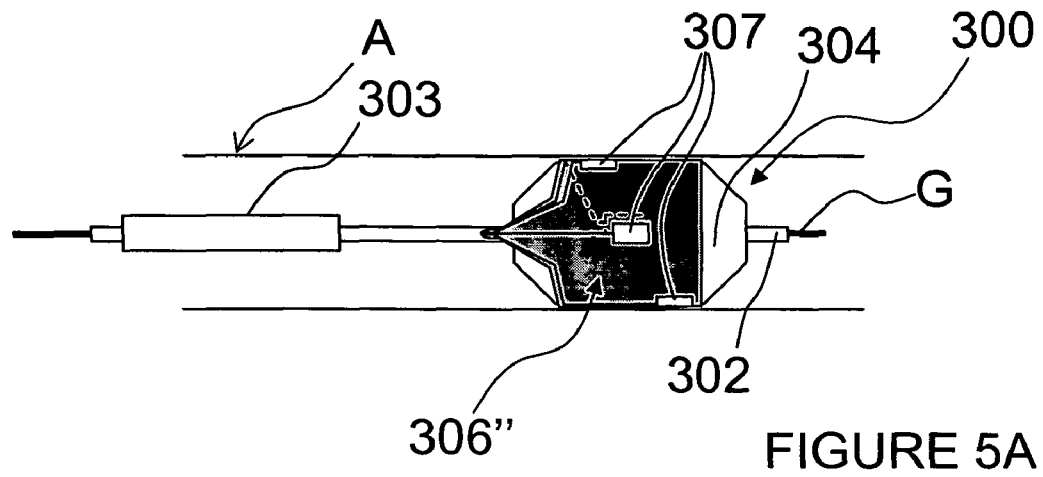
FIGS. 5A and 5B are schematic side views, partially in section, illustrating still further alternative methods and apparatus for non-continuous circumferential treatments.
Figure 5B:
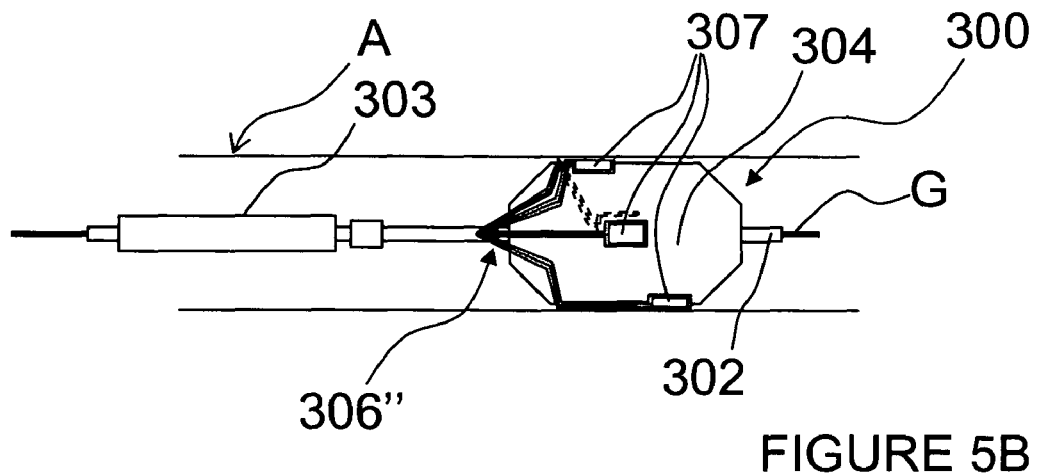

FIGS. 5A and 5B describe additional apparatus and methods for non-continuous circumferential treatment without having to reposition electrodes or other energy delivery elements. As seen in FIGS. 5A and 5B, the apparatus 300 has an electrode element 306" that comprises a flex circuit coupled to or positioned about the positioning element 304. The flex circuit is electrically coupled to the field generator 50 by wires that extend through or along the catheter 302 or by wireless transmission. In FIG. 5A, the flex circuit comprises a collapsible cylinder positioned about the positioning element 304. In FIG. 5B, the flex circuit comprises individual electrical connections for each electrode 307, which may facilitate collapse of the flex circuit for delivery and retrieval. As with the electrodes of apparatus 400 of FIG. 4, the electrodes 307 of FIG. 7 are spaced at multiple lengthwise positions relative to the positioning element and the blood vessel. The electrodes may be operated as described previously to achieve a non-continuous circumferential treatment. As the electrodes 307 illustratively are positioned at three different lengthwise positions, the non-continuous circumferential treatment may, for example, be formed via superimposition of three treatment zones (one at each lengthwise position within the blood vessel).

With any of the embodiments described herein, during delivery of the electric field (or of other energy), blood within the vessel may act as a thermal sink (either hot or cold) for conductive and/or convective heat transfer for removing excess thermal energy from the non-target tissue (such as the interior wall of the vessel), thereby protecting the non-target tissue. This effect may be enhanced when blood flow is not blocked during energy delivery, for example, as in the embodiments of FIGS. 3 and 4 (it should be understood that a variation of the embodiments of FIGS. 5 may provide for blood flow; for example, the electrode(s) may be brought into contact with the vessel wall via an expandable basket rather than via an inflatable balloon). Use of the patient's blood as a thermal sink is expected to facilitate delivery of longer or higher energy treatments with reduced risk of damage to the non-target tissue, which may enhance the efficacy of the treatment at the target tissue, for example, at target neural fibers.

In addition or as an alternative to utilizing the patient's blood as a thermal sink, a thermal fluid (hot or cold) may be injected, infused or otherwise delivered into the vessel to remove excess thermal energy and protect the non-target tissues. This method of using an injected thermal fluid to remove excess thermal energy from non-target tissues to protect the non-target tissues from thermal injury during therapeutic treatment of target tissues may be utilized in body lumens other than blood vessels. The thermal fluid may, for example, comprise chilled or room temperature saline (e.g., saline at a temperature lower than the temperature of the vessel wall during the therapy delivery). The thermal fluid may, for example, be injected through the device catheter or through a guide catheter. The thermal fluid injection may be in the presence of blood flow or with flow temporarily occluded. Occlusion of flow in combination with thermal fluid delivery may facilitate better control over the heat transfer kinetics along the non-target tissues, as well as optional injection of the fluid from a downstream location.

Figure 6A:
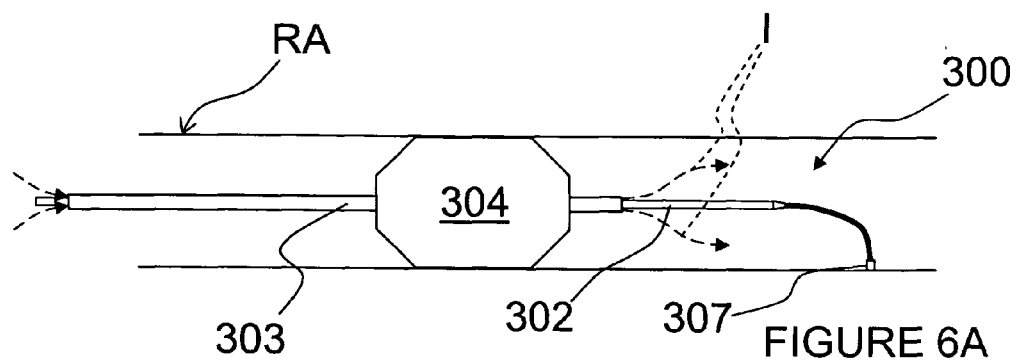
FIGS. 6A and 6B are schematic side views, partially in section, illustrating additional alternative methods and apparatus for non-continuous circumferential treatments.

Referring now to FIGS. 6, another embodiment of the apparatus 300 is described that comprises optional flow occlusion and thermal fluid injection. The optional occlusion/positioning element 304 illustratively is coupled to the guide catheter 303, and the catheter 302 may be repositioned relative to the guide catheter to reposition the electrode(s) 307, optionally without re-establishing flow through the vessel. In FIGS. 6, the alternative electrode element 306'" is self-expanding, and/or is shapeable (e.g., is formed from a spring steel) by a medical practitioner to provide a desired profile for positioning of the electrode(s) 307 into contact with the vessel wall.

The catheter 302 may be advanced within the renal artery RA in a reduced profile delivery configuration. Once properly positioned, the electrode element 306'" may self-expand (or may be actively expanded) to bring the electrode(s) 307 into contact with the vessel wall, for example, by removing the electrode element from the lumen of the guide catheter. The element 304 also may be expanded (before, during or after expansion of the electrode element) in order to properly position the electrode within the vessel and/or to occlude blood flow within, e.g., the renal artery. An electric field, such as a monopolar electric field, may be delivered via the electrode(s) 307, e.g., between the electrode(s) and an external ground (not shown; per se known). The electric field may, for example, comprise a pulsed or continuous RF electric field that thermally induces neuromodulation (e.g., necrosis or ablation) in the target neural fibers. The therapy may be monitored and/or controlled, for example, via data collected with thermocouples or other sensors, e.g., impedance sensors.

In order to increase the power or duration of the treatment that may be delivered without damaging non-target tissue of the vessel wall to an unacceptable extent, a thermal fluid infusate I may be injected, e.g., through the guide catheter 303 to cool (heat) the non-target tissue, thereby mitigating damage to the non-target tissue. The infusate may, for example, comprise chilled saline that removes excess thermal energy (hot or cold) from the wall of the vessel during thermal RF therapy.

Convective or other heat transfer between the non-target vessel wall tissue and the infusate I may facilitate cooling (heating) of the vessel wall at a faster rate than cooling (heating) occurs at the target neural fibers. This heat transfer rate discrepancy between the wall of the vessel and the target neural fibers may be utilized to modulate the neural fibers with reduced damage to the vessel wall. Furthermore, when utilizing a pulsed therapy, the accelerated heat transfer at the wall relative to the neural fibers may allow for relatively higher power or longer duration therapies (as compared to continuous therapies), due to the additional time between pulses for protective cooling at the vessel wall. Also, the interval between pulses may be used to monitor and/or control effects of the therapy.

Figure 6B:
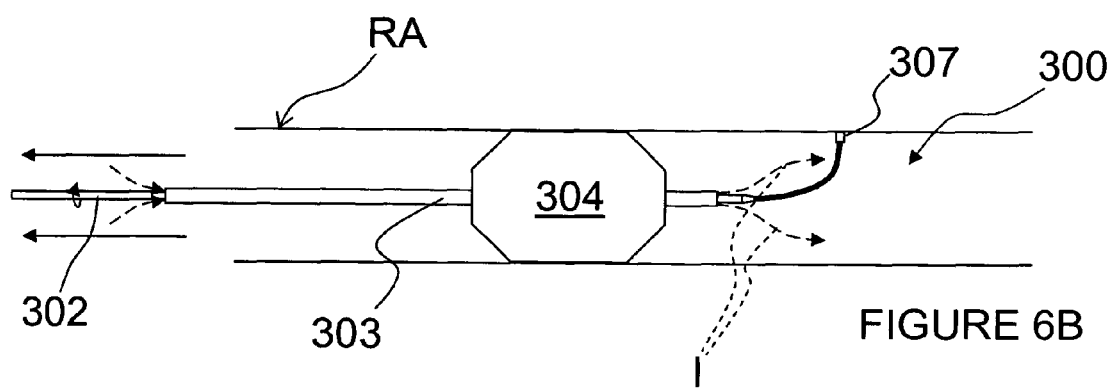

Referring now to FIG. 6B, treatment at additional angular and lengthwise positions relative to the vessel wall may be achieved by rotation and lengthwise repositioning of the catheter 302. This may be repeated at as many lengthwise and/or angular positions as desired by the medical practitioner. The treatment(s) at each individual lengthwise position preferably do not form a continuous circumferential lesion normal to the vessel wall, while superimposition of the treatments at multiple such lengthwise positions preferably forms a non-continuous, partially or fully circumferential lesion, as described previously.

Figure 7A:
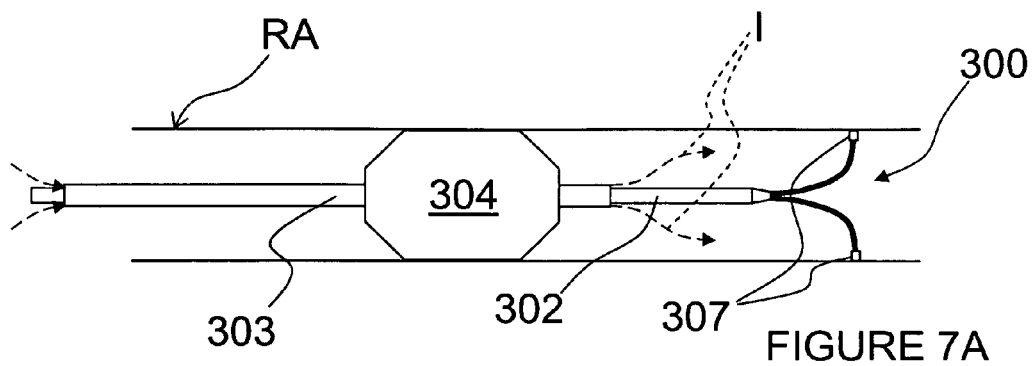
FIG. 7A and 7B are schematic side views, partially in section, illustrating alternative embodiments of the apparatus and methods of FIGS. 6.
Figure 7B:
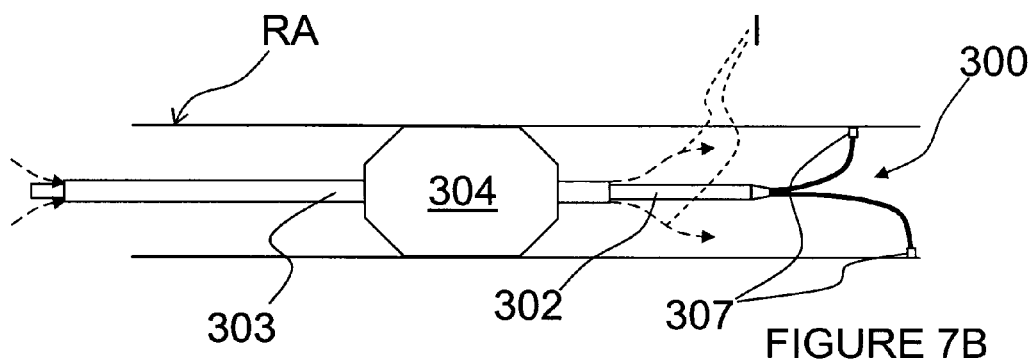

In the embodiment of the FIGS. 6, the apparatus illustratively comprises a single electrode 307. However, multiple such electrodes optionally may be provided at multiple, angularly-offset positions, as in FIG. 7A. This may reduce the number of lengthwise positions where treatment needs to be conducted in order to achieve the non-continuous, substantially circumferential treatment of the present invention. In addition or as an alternative to angular offsetting, the electrodes optionally may be offset lengthwise from one another, such that treatment at the multiple lengthwise positions may be achieved concurrently or sequentially without necessitating lengthwise repositioning of the electrodes. FIG. 7B illustrates an embodiment of apparatus 300 having multiple electrodes that are offset from one another both angularly and lengthwise. In such an embodiment, the relative angular and lengthwise positions of the electrodes may be fixed or may be dynamically alterable by the medical practitioner.

Figure 8:
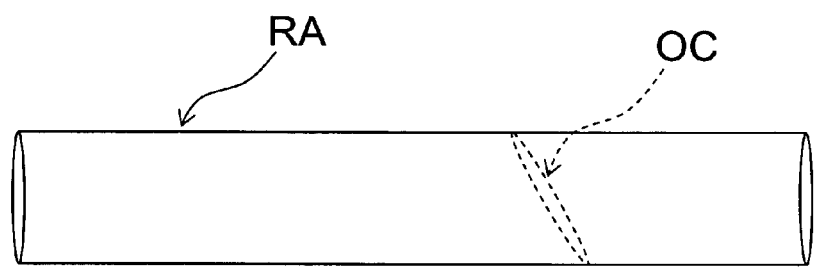
FIG. 8 is a schematic side view, illustrating a non-continuous circumferential treatment that is oblique to the lengthwise axis of the patient's vasculature.

As described herein, a continuous circumferential lesion is a circumferential lesion that is substantially continuous in a radial plane normal to the vessel or luminal wall. Conversely, a non-continuous circumferential lesion may be non-continuous relative to a normal radial plane, but substantially continuous along an oblique plane of the vasculature that is not normal to the vessel wall. For example, as seen in dotted profile in FIG. 8, an oblique circumferential treatment OC may be achieved within the patient's vasculature, e.g. the patient's renal artery RA, without formation of a continuous circumferential treatment relative to a normal radial plane of the vasculature. The previously-described apparatus and methods of FIGS. 5 may, for example, form such an oblique circumferential treatment OC.

Figure 9A:
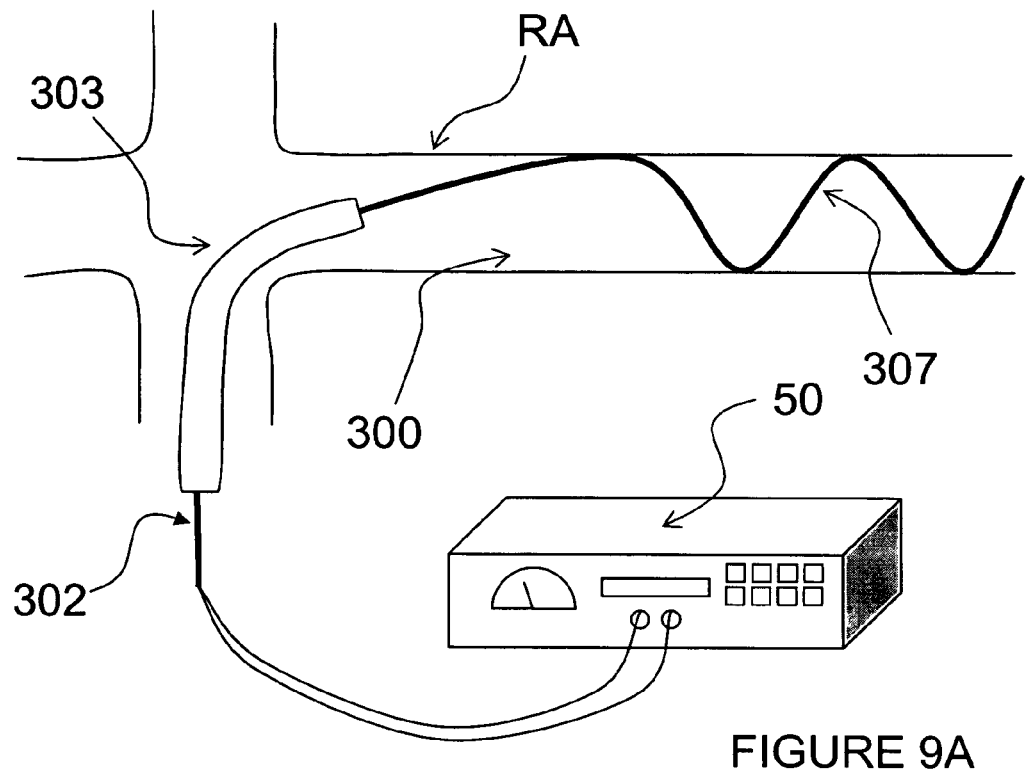
FIGS. 9A and 9B are schematic side views, partially in section, illustrating intravascular methods and apparatus for oblique circumferential treatment.
Figure 9B:
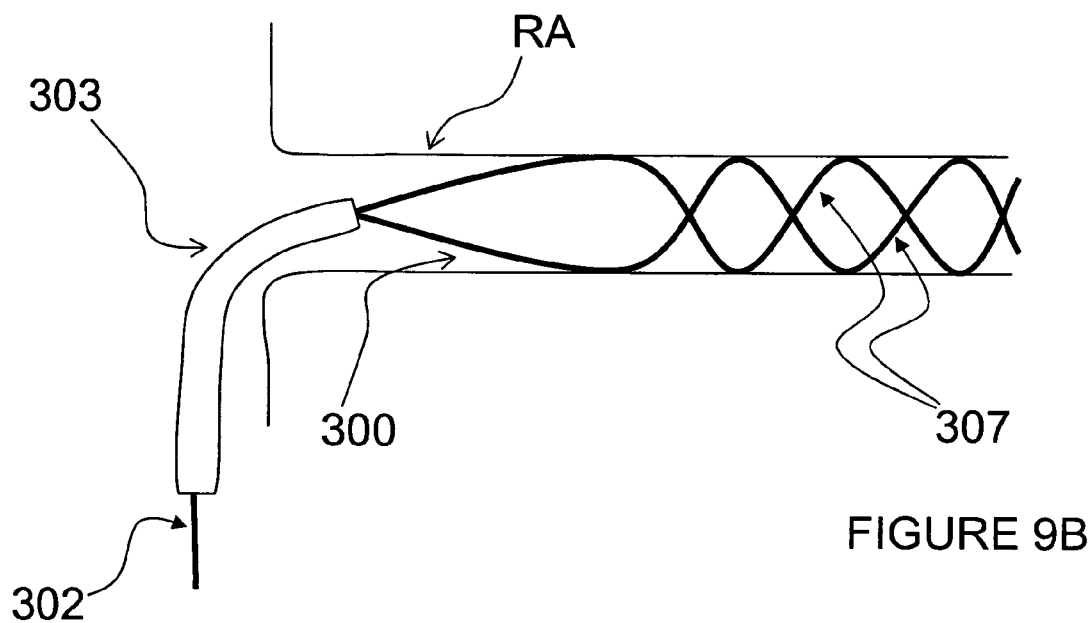

FIGS. 9A and 9B illustrate additional methods and apparatus for achieving such oblique circumferential treatments. In FIG. 9A, the apparatus 300 comprises a spiral or helical electrode element 307 that contacts the wall of the vasculature along one or more partial or complete oblique circumferences. The electrode element 307 may comprise a single continuous electrode over all or a portion of the spiral for formation of a continuous oblique treatment, and/or may comprise multiple discrete electrodes positioned along the spiral, e.g., for formation of a non-continuous circumferential treatment relative to both oblique and the normal planes of the vessel. Regardless of the form of the electrode element 307, the treatment zone(s) formed with the electrode may form a non-continuous circumferential treatment relative to the normal radial plane of the vasculature.

FIG. 9B illustrates an alternative embodiment of the apparatus and methods of FIG. 9A, in which the electrode element 307 comprises a double helix. This may facilitate formation of multiple, non-continuous treatment zones along one or more normal radial planes of the vessel. Continuous or non-continuous oblique treatments also may be achieved, while non-continuous normal circumferential treatments are achieved via superimposition of treatment at multiple locations (either discrete or continuous) along a lengthwise segment of the vasculature.

Figure 10A:
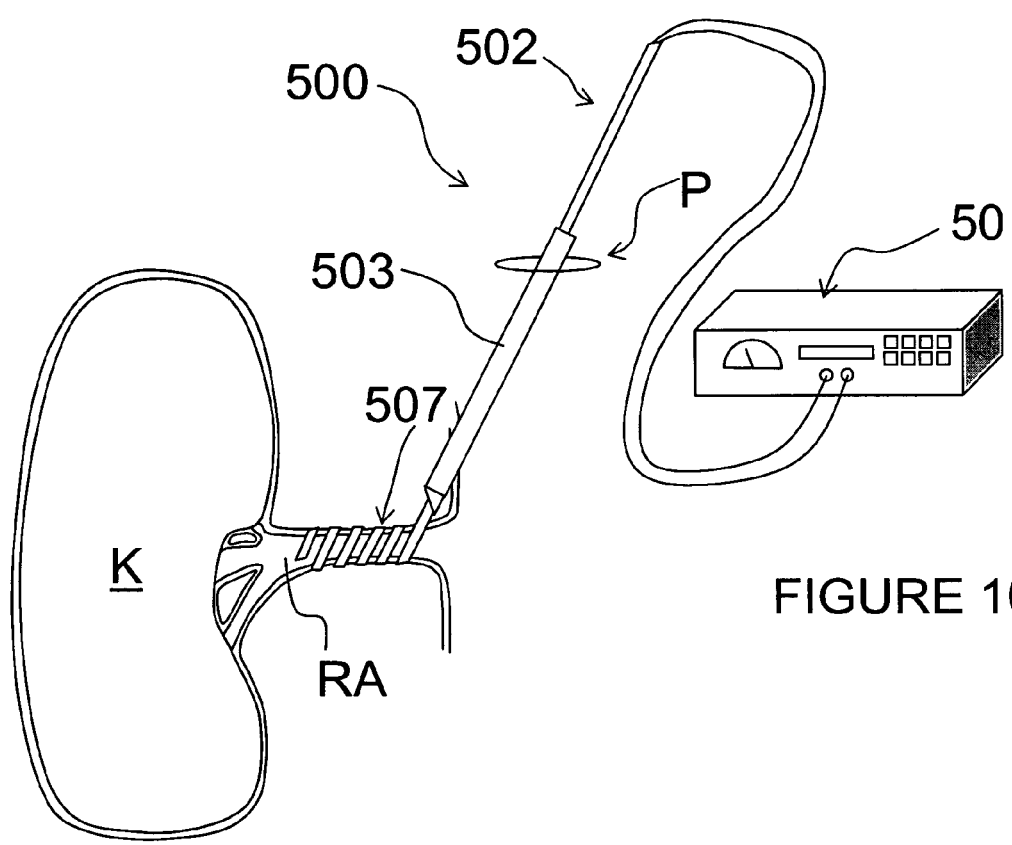
FIGS. 10A and 10B are schematic side views, partially in section, illustrating extravascular embodiments of methods and apparatus for non-continuous circumferential treatment of a body lumen, illustratively oblique circumferential treatment.
Figure 10B:
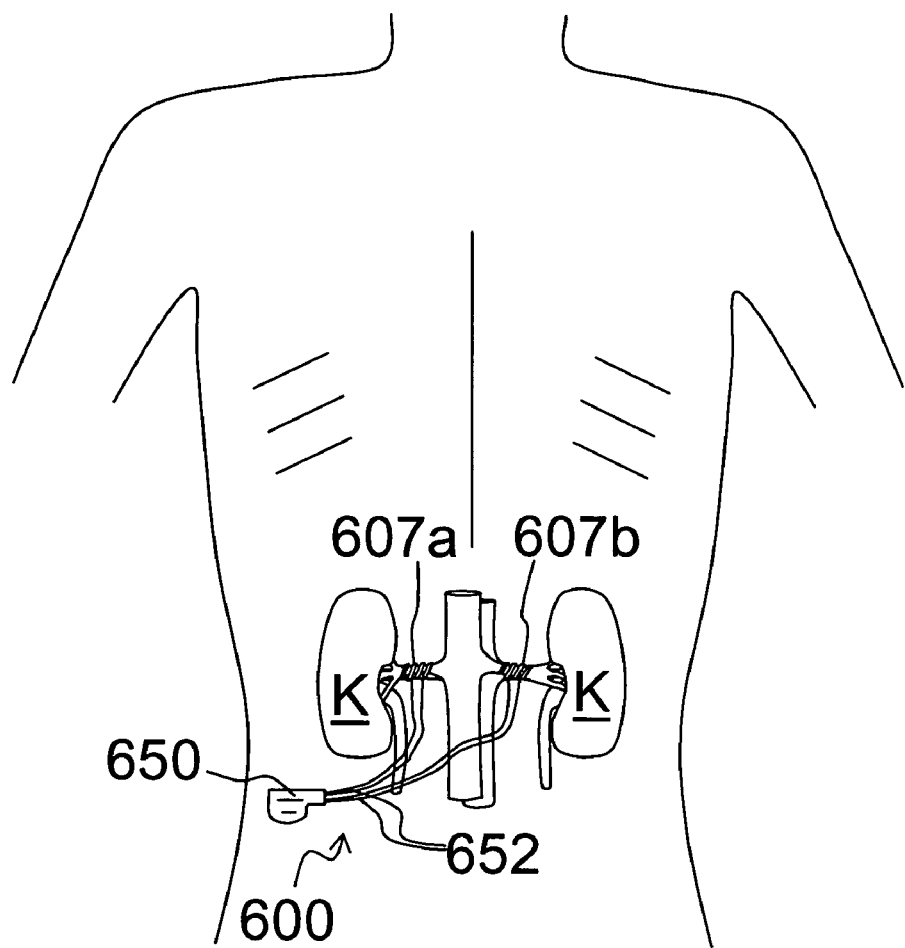

Referring now to FIGS. 10A and 10B, extravascular variations are described. FIG. 10A illustrates a percutaneous or transcutaneous extravascular variation having electrode(s) configured for temporary placement about the renal vasculature of the patient. FIG. 10B illustrates an implantable extravascular variation configured for prolonged placement within the patient. As will be apparent to those of skill in the art, a composite extravascular variation also may be provided having some elements configured for temporary placement and some elements configured for prolonged placement. In one such variation, one or more electrodes may be implanted within the patient, and a pulse generator or battery charging unit, etc., may be placed external to the patient and/or may be placed within the patient only temporarily during treatment, diagnostics, charging, etc.

The apparatus and methods of FIGS. 10 illustratively are configured for formation of partially or completely continuous oblique circumferential treatments that are non-continuous relative to normal radial planes of the patient's vasculature. However, it should be understood that alternative extravascular embodiments may comprise non-continuous normal circumferential treatments that are non-continuous about both the normal and lengthwise dimensions of the vasculature, as opposed to just the normal dimension, i.e., that are also non-continuous about the oblique section. See, for example, the treatments defined by the apparatus and methods of FIGS. 2-7.

In FIG. 10A, apparatus 500 comprises needle or trocar 503 that forms percutaneous access site P. Catheter 502 is advanced through the trocar into proximity of the patient's renal artery RA. Electrode element 507 spirals about the renal artery for formation of an oblique circumferential treatment, as described with respect to FIG. 9A. Electrode element 507 is electrically coupled to field generator 50 for delivery of a desired electrical treatment. The apparatus 500 optionally may be removed from the patient, and the access site P closed, after formation of the oblique circumferential treatment.

FIG. 10B illustrates an extravascular embodiment that is fully implantable and illustratively is configured for bilateral treatment of nerves innervating both of the patient's kidney. It should be understood that any of the previously described embodiments also may be utilized for bilateral treatment, either concurrently or sequentially. Apparatus 600 comprises first and second spiral electrode elements 607a and 607b that spiral about the patient's renal arteries. The electrode elements are electrically coupled to implantable field generator 650, e.g., via tunneled leads 652, for formation of the previously described oblique circumferential treatment.

FIGS. 2-7 and 9-10 illustratively describe electrical methods and apparatus for circumferential treatment without formation of a continuous circumferential lesion positioned normal to the lengthwise axis of the patient's vasculature. However, it should be understood that alternative energy modalities, including magnetic, mechanical, thermal, chemical, nuclear/radiation, fluid, etc., may be utilized to achieve the desired circumferential treatment without circumferential lesion. Furthermore, although FIGS. 2-7 and 9 illustratively comprise fully intravascular positioning of the apparatus, it should be understood that all or a portion of the apparatus in any of the embodiments may be positioned extravascularly as in FIGS. 10, optionally via implantation and/or via an intrato-extravascular approach.

Although preferred illustrative variations of the present invention are described above, it will be apparent to those skilled in the art that various changes and modifications may be made thereto without departing from the invention. For example, although in the described embodiments of FIGS. 2-4 non-continuous circumferential treatment is achieved via superimposition of treatment at two locations, it should be understood that treatment at more than two locations may be superimposed to achieve the circumferential treatment, as described with respect to FIGS. 5A and 5B. Furthermore, although in the described embodiments the methods are conducted in a blood vessel, it should be understood that treatment alternatively may be conducted in other body lumens. It is intended in the appended claims to cover all such changes and modifications that fall within the true spirit and scope of the invention.

We claim:

1. A method for non-continuous circumferential treatment of a renal blood vessel of a patient, the method comprising:

positioning an energy delivery element at least proximate to a wall of the renal blood vessel;

delivering energy from the energy delivery element to less than a full radial circumference of the renal blood vessel at a first lengthwise position relative to the renal blood vessel to form a first treatment zone, wherein the first treatment zone includes a first lesion; and delivering energy from the energy delivery element to less than a full radial circumference of the renal blood vessel at a second lengthwise position relative to the renal blood vessel to form at least a second treatment zone, wherein the second treatment zone includes a second lesion, and wherein the first lengthwise position and the second lengthwise position are spaced apart from one another along a lengthwise dimension of the renal blood vessel, and further wherein the first and second lesions do not overlap.

2. The method of claim 1, wherein delivering energy at the second lengthwise position further comprises re-positioning the energy delivery element relative to the renal blood vessel of the patient.

3. The method of claim 1, wherein positioning the energy delivery element at least proximate to the renal blood vessel of the patient further comprises positioning the energy delivery element at least proximate to a blood vessel of the patient.

4. The method of claim 3, wherein positioning the energy delivery element at least proximate to the blood vessel of the patient further comprises positioning the energy delivery element within a blood vessel of the patient.

5. The method of claim 3, wherein positioning the energy delivery element at least proximate to the blood vessel of the patient further comprises positioning the energy delivery element external to the blood vessel of the patient.

6. The method of claim 3 further comprising blocking blood flow within the blood vessel during the energy delivery.

7. The method of claim 3, wherein positioning the energy delivery element at least proximate the blood vessel of the patient further comprises positioning the energy delivery element at least proximate a renal vasculature of the patient.

8. The method of claim 1, wherein positioning the energy delivery element at least proximate to the renal blood vessel of the patient further comprises positioning the energy delivery element within the renal blood vessel of the patient.

9. The method of claim 8, wherein positioning the energy delivery element within the renal blood vessel of the patient further comprises contacting the wall of the renal blood vessel with the energy delivery element.

10. The method of claim 8, wherein positioning the energy delivery element within the renal blood vessel of the patient further comprises passing the energy delivery element across the wall of the renal blood vessel prior to the energy delivery.

11. The method of claim 1, wherein delivering energy from the energy delivery element at the first and second lengthwise positions further comprises repositioning the energy delivery element.

12. The method of claim 1, wherein positioning the energy delivery element in proximity to the renal blood vessel further comprises positioning an energy delivery element comprising energy delivery sub-elements that are spaced lengthwise and angularly relative to one another.

13. The method of claim 12, wherein delivering energy at the first and at least second lengthwise positions further comprises delivering energy with the lengthwise- and angularly-spaced energy delivery sub-elements.

14. The method of claim 13, wherein delivering energy with the energy delivery sub-elements further comprises concurrently delivering energy at the first and the at least second lengthwise positions.

15. The method of claim 13, wherein delivering energy with the energy delivery sub-elements further comprises sequentially delivering energy at the first and the at least second lengthwise positions in any desired order.

16. The method of claim 1, wherein positioning the energy delivery in proximity to the renal blood vessel of the patient further comprises positioning the energy delivery element in proximity to multiple renal blood vessels of the patient.

17. The method of claim 1, wherein positioning the energy delivery element in proximity to the renal blood vessel further comprises positioning at least one electrode in proximity to the renal blood vessel, and
wherein delivering energy with the energy delivery element further comprises delivering an electric field from the at least one electrode.

18. The method of claim 17 further comprising attaching an external ground to an exterior of the patient,
wherein delivering the electric field further comprises delivering the electric field in a monopolar fashion between the at least one electrode and the external ground.

19. A method for treatment, the method comprising:
positioning an energy delivery element at a first lengthwise and angular position relative to a renal blood vessel of a patient;
delivering energy from the energy delivery element to less than a full circumference of the renal blood vessel at the first lengthwise and angular position to form a first treatment zone, wherein the first treatment zone includes a first lesion;
repositioning the energy delivery element to a second lengthwise and angular position relative to the renal blood vessel that is different than the first lengthwise and angular position; and
delivering energy from the energy delivery element to less than a full circumference of the renal blood vessel at the second lengthwise and angular position to form a second treatment zone, wherein the second treatment zone includes a second lesion spaced apart from and out of contact with the first lesion.

20. The method of claim 19, wherein a composite treatment zone formed via superimposition of the first treatment zone and the second treatment zone comprises a non-continuous, circumferential treatment zone.

21. A method for treating a patient, the method comprising:
delivering energy to a first treatment zone at an inner wall of a renal blood vessel and to a second treatment zone at the wall of the renal blood vessel, wherein the first treatment zone has a discrete, non-continuous first lesion at a first radial plane and the second treatment zone has a discrete, non-continuous second lesion at a second radial plane spaced apart from the first radial plane, and wherein the first lesion does not come into contact with the second lesion; and
affecting neural tissue outside of the inner wall of the renal blood vessel.

22. The method of claim 21 wherein affecting neural tissue outside of the inner wall comprises blocking neural activity across the neural tissue.

* * * * *